United States Patent
Grillari et al.

(10) Patent No.: US 9,150,855 B2
(45) Date of Patent: Oct. 6, 2015

(54) METHODS FOR DIAGNOSING BONE OR CARDIOVASCULAR DISORDERS

(71) Applicant: UNIVERSITÄT FÜR BODENKULTUR WIEN, Vienna (AT)

(72) Inventors: Johannes Grillari, Bisamberg (AT); Elisabeth Schraml, Vienna (AT); Klaus Fortschegger, Maria Anzbach (AT); Regina Grillari, Bisamberg (AT)

(73) Assignee: UNIVERSITÄT FÜR BODENKULTUR WIEN, Vienna (AT)

( * ) Notice: Subject to any disclaimer, the term of this patent is extended or adjusted under 35 U.S.C. 154(b) by 0 days.

(21) Appl. No.: 14/094,772

(22) Filed: Dec. 2, 2013

(65) Prior Publication Data

US 2014/0162265 A1 Jun. 12, 2014

Related U.S. Application Data

(62) Division of application No. 13/699,272, filed as application No. PCT/EP2011/058379 on May 23, 2011.

(30) Foreign Application Priority Data

May 21, 2010 (EP) ..................................... 10163604

(51) Int. Cl.
| | |
|---|---|
| C12N 15/113 | (2010.01) |
| A61K 9/127 | (2006.01) |
| A61K 31/7105 | (2006.01) |
| C12Q 1/68 | (2006.01) |

(52) U.S. Cl.
CPC .............. *C12N 15/113* (2013.01); *A61K 9/127* (2013.01); *A61K 31/7105* (2013.01); *C12N 15/1138* (2013.01); *C12Q 1/6881* (2013.01); *C12N 2310/113* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 5,998,424 A | 12/1999 | Galemmo, Jr. et al. | |
| 7,683,036 B2 | 3/2010 | Esau et al. | |
| 2006/0167087 A1 | 7/2006 | Greve et al. | |
| 2009/0075258 A1* | 3/2009 | Latham et al. | 435/6 |
| 2009/0291906 A1 | 11/2009 | Esau et al. | |
| 2010/0004320 A1 | 1/2010 | Elmen et al. | |
| 2013/0210883 A1 | 8/2013 | Grillari et al. | |

FOREIGN PATENT DOCUMENTS

| | | |
|---|---|---|
| WO | WO 2004/063169 A1 | 7/2004 |
| WO | WO2007112754 | 10/2007 |
| WO | WO 2008/013963 A2 | 1/2008 |
| WO | WO 2010/115825 A2 | 10/2010 |
| WO | WO 2011/072241 A1 | 6/2011 |

OTHER PUBLICATIONS

International Search Report, PCT/EP2011/058379, mailed Sep. 23, 2011.
Jones, S.W. Ph.D. et al., "The Identification of differentially expressed microRNA in osteoarthritic tissue that modulate the production of TNF-alpha and MMP13", Osteoarthritis and Cartilage, vol. 17, pp. 464-472 (2009).
Sun, F. et al., "Characterization of function and regulation of miR-24-1 and miR-31", Biochemical and Biophysical Research Communications, vol. 380, pp. 660-665 (2009).
Valastyan, S. et al., "A Pleiotropically Acting MicroRNA, miR-31, Inhibits Breast Cancer Metastasis", Cell, vol. 137, pp. 1032-1046 (2009).
Carini et al., "Nonpeptide Angiotensin II Receptor Antagonists: N-[(Benzyloxy)benzyl]imidazoles and Related Compounds as Potent Antihypertensives," J. Med. Chem., 1990, 33:1330-1336.
Chodorowski-Kimmes et al., "Synthesis of Bridging Electron Transfer Donor Ligands," Tetrahedron Letters, 1997, 38(21):3659-3662.
Dressen et al., "Preparation and Optimization of a Series of 3-Carboxamido-5-phenacylaminopyrazole Bradykinin B1 Receptor Antagonists," J. Med. Chem., 2007, 50:5161-5167.
Grovenstein, Jr. et al., "Carbanions. 21. Reactions of 2- and 3-p-Biphenylylalkyl Chlorides with Alkali Metals. Preparation of Labile Spiro Anions," J. Org. Chem., 1982, 47:2928-2939.
Kitamura et al., "Heterogeneous Pd/C-catalyzed ligand-free Suzuki Miyaura coupling reaction using aryl boronic esters," Tetrahedron, 2007, 63:10596-10602.
Mamalis et al., "142. Some Heterocyclic N-Oxides," Journal of the Chemical Society, 1950, Part I, pp. 703-711.
Mayer et al., "Development of small-molecule inhibitors targeting adipose triglyceride lipase," Nature Chemical Biology, Oct. 2013, 9(12):785-787.
Seki et al., "Studies on Hypolipidemic Agents. II. Synthesis and Pharmacological Properties of Alkylpyrazole Derivatives," Chem. Pharm. Bull.,1984, 32(4)1 568-1577.
Walker et al., "Coupling Catalyst. A Rationally Designed Universal Catalyst for Suzuki-Miyaura Coupling Processes," Agnew. Chem. Im. Ed., 2004, 43:1871-1876.
U.S. Appl. No. 13/699,272, Non-Final Office Action (Restriction Requirement), Feb. 22, 2013.
U.S. Appl. No. 13/699,272, Non-Final Office Action, Mar. 11, 2014.

* cited by examiner

Primary Examiner — Kimberly Chong
(74) Attorney, Agent, or Firm — Michael Fedrick; Loza & Loza, LLP

(57) ABSTRACT

The invention relates to methods for diagnosing bone disorders and/or cardiovascular disorders in a subject, by contacting a biological sample from the subject with (a) a nucleic acid molecule which hybridizes to miR-31 or its 5 or 3' isoforms or variants, or (b) an agent that binds to miR-31 or its 5' or 3' isoforms or variants; detecting and evaluating the hybridization signal of the nucleic acid molecule or agent with a polynucleotide or said miR-31 or its 5' or 3' isoforms or variants; and comparing the detected and evaluated hybridization or binding signal with that of a control sample, wherein a stronger hybridization signal or a stronger binding signal in the sample of the subject compared to that of the control sample is indicative for a risk of developing or having a bone disorder and/or cardiovascular disorder.

12 Claims, 20 Drawing Sheets

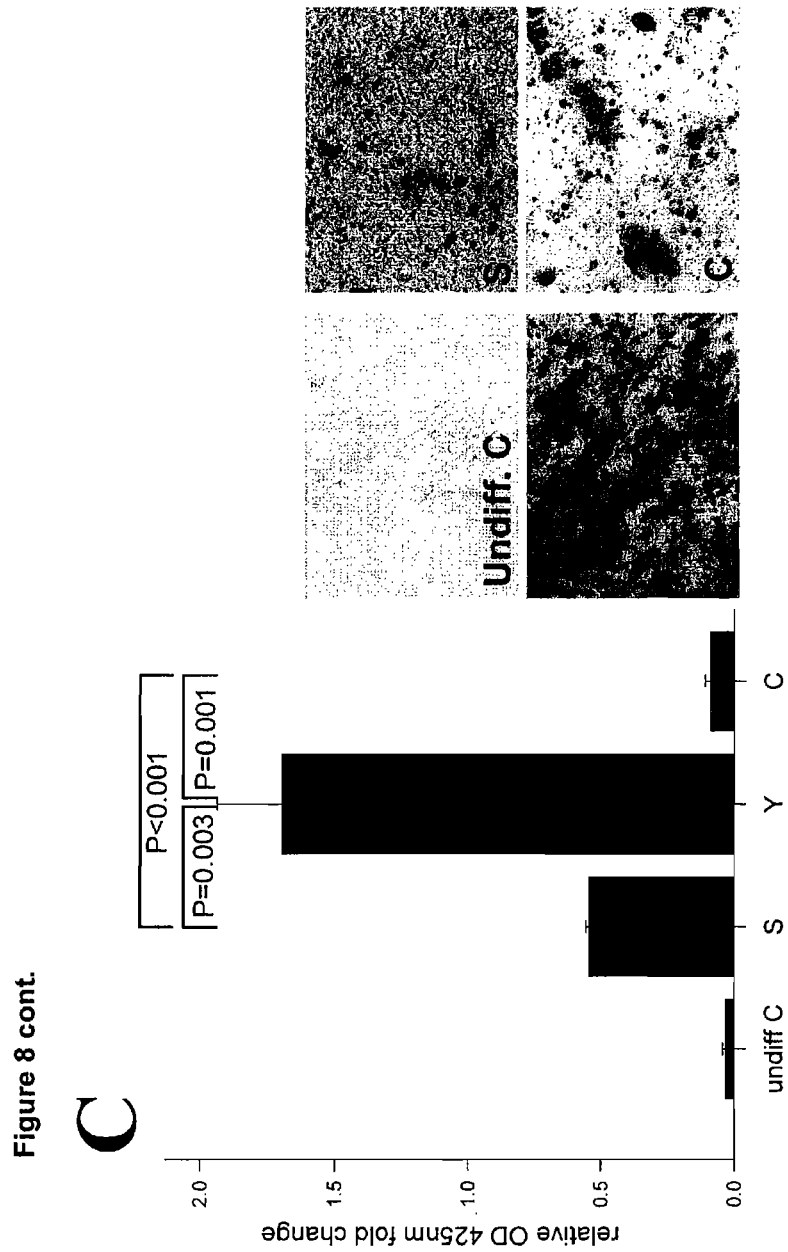

METHODS FOR DIAGNOSING BONE OR CARDIOVASCULAR DISORDERS

CROSS-REFERENCE TO RELATED APPLICATIONS

This application is a division of application Ser. No. 13/699,272 filed Nov. 20, 2012, which is the U.S. national stage of International application no. PCT/EP2011/058379 filed May 23, 2011, which claims priority of European application no. 1016064.1 filed May 21, 2010.

BACKGROUND

The present invention relates to compositions comprising an antagonist/inhibitor of a polynucleotide, said polynucleotide to be inhibited being capable of decreasing or suppressing expression of FZD3 (Frizzled-3) or a biologically active derivative thereof for use in treating or preventing bone disorders and/or cardiovascular disorders. Such bone disorders comprise, inter alia, osteoporosis, osteopenia, bone fracture, bone cancer, as well as impaired bone homeostasis. Cardiovascular diseases to be treated by the compounds of the present invention may be selected from the group consisting of infarction, stroke, hypertension, thrombosis, vascular stenosis, coronary syndromes, vascular dementia, heart failure, renal failure, stress-related carciovascular disorders, and atherosclerosis. Preferred compounds to be used in these medical interventions are antagonistic compounds, like nucleic acid molecules, directed to polynucleotides that are capable of decreasing or suppressing expression of FZD3 or a biologically active derivative thereof. An example of such a polynucleotide that needs to be antagonized is miR-31 or its 5' or 3' isoforms or variants. Also, the present invention relates to methods for and compositions for use in diagnosing bone disorders and/or cardiovascular disorders. Compounds to be used in these diagnostic methods may be compounds (like primers and probes) that are capable of detecting such a polynucleotide that is capable of decreasing or suppressing expression of FZD3 or a biologically active derivative thereof. miR-31 (or miR-31 or its 5' or 3' isoforms or variants) is, in accordance with this invention, a polynucleotide that is capable of decreasing or suppressing expression of FZD3.

Accumulation of damage in cells and tissues has been accepted as one of the major driving forces of aging and age related diseases (Kirkwood, Cell (2005), 120: 437-474). One of the repair systems on tissue level that counteracts this functional decline are adult stem and progenitor cells. Their ability to self-renew and differentiate is essential for homeostasis of tissues and organs. As adult human stem and progenitor cells with high differentiation potential have been identified in different tissues of the human body they would represent a pool of cells that should maintain high levels of tissue functionality. However, their function also declines with age (Rando, Nature (2006), 441: 1080-1086). The old systemic environment has been identified to contain factors that either fail to promote or actively inhibit successful tissue regeneration when tested in a parabiosis mouse model (Conboy, Nature (2005), 433: 760-764), while factors contained in the systemic environment of young animals promote successful tissue regeneration (Matsumoto, Eur Heart J (2009), 30: 346-355).

Visceral fat accretion is among the hallmarks of aging in humans (Huffman, Biochem Biophys Acta (2009), 1790: 1117-1123), while osteogenic differentiation potential of ASCs decreases with age. This decrease is not due to a loss of osteogenic precursors (Zhu, J Tissue Eng Regen Med (2009), 3: 290-301), suggesting that factors altering the cellular behaviour are involved. Furthermore, ASCs and endothelial cells are linked in vivo since preadipocytes within adipose tissue depots and endothelial cells exhibit a close relationships (Hausman, J Anim Sci (2004), 82: 925-934), supporting a paracrine relationship between these cell types.

However, the source of these factors altering the cellular behaviour was unknown so far and only scarce knowledge is available on the identity of these factors, where Wnt and TGF-β signalling seem to be involved (Carlson, Aging Cell (2009), 8: 676-689). Besides various glands, one source of secretion into the blood stream are endothelial cells per se and during older age, senescent endothelial cells, since they accumulate during aging in vivo, especially at sites of atherosclerosis (Erusalimsky, Handb Exp Pharmacol (2006), 213-248; Erusalimsky, Exp Physiol (2009), 94: 299-304); Minamino, Circ Res (2007), 100: 15-26). Several proteins that increase with senescence (Chang, Exp Cell Res (2005), 309: 121-136) have been identified, among them interleukin 8 that is found at up to 50-fold higher levels in the supernatants of senescent endothelial cells (Hampel, Exp Gerontol (2006), 41: 474-481).

One of the transport mechanisms in blood has been described: various factors are packaged into exosomes, membrane-coated particles that are secreted via exocytosis and play a role in cell-cell or organ-organ communication by fusion with cells of target tissues (Caby, Int Immunol (2005), 17: 879-887). Exosomes, 40-100 nm in size, are membrane vesicles of endosomal origin that are released into the extracellular environment. They can act on intercellular communication by allowing exchange of proteins, lipids, and also mRNA and miRNAs between cells (Valadi, Nat Cell Biol (2007), 9: 654-659; Viaud, PLoS One (2009), 4: e4942). The contained factors like miRNAs, mRNAs and proteins then influence the behaviour of the target cells. Examples are endothelial progenitor cell derived exosomes that induce angiogenesis in endothelial cells upon uptake (Deregibus, Blood (2007), 110: 2440-2448), endothelial-derived exosomes in patients with pulmonary arterial hypertension (Bakouboula, Am J Respir Crit Care Med (2008), 177: 536-543), ovarian carcinoma and glioblastoma cells that release exosomes and change the tissue microenvironment in favour of tumor progression (Keller, Cancer Lett (2009), 278: 73-81; Skog, Nat Cell Biol (2008), 10: 1470-1476). Especially exosomes released from tumour cells, which carry antigenic molecules recognized by T cells, has suggested as a cell free antigen source for anticancer vaccines (Escudier, J Transl Med (2005), 3: 10; Iero, Cell Death Differ (2008), 15: 80-88; Morse, J Transl Med (2005), 3: 9; Viaud, Horm Metab Res (2008), 40: 82-88; Viaud, PLoS One (2009), 4: e49429).

However, mechanisms and factors involved in tissue regeneration or in inhibiting the same are still poorly understood and influencing the impact of such factors on tissue regeneration is hardly possible.

This technical problem has been solved by the embodiments provided herein and the solutions provided in the claims.

SUMMARY OF THE INVENTION

Accordingly, the present invention provides for a composition comprising an inhibitor of a polynucleotide, said polynucleotide to be inhibited being capable of decreasing or suppressing expression of frizzled 3 (FZD3) or a biologically active derivative thereof for use in treating or preventing bone disorders and/or cardiovascular disorders in a subject as will be further detailed and exemplified herein below. Also, the present invention provides for a method for treating or preventing bone disorders and/or cardiovascular disorders in a subject comprising administering an effective amount of a composition comprising an inhibitor of a polynucleotide, said polynucleotide to be inhibited being capable of decreasing or suppressing expression of FZD3 or a biologically active derivative thereof. A polynucleotide to be inhibited in context of this medical intervention (i.e. the herein disclosed medical/pharmaceutical uses) and the methods of treating/preventing a disorder as provided herein may be miR-31 or its 5' or 3' isoforms or variants. Furthermore, the present invention provides for a composition for use in and a method for diagnosing bone disorders and/or cardiovascular disorders in a subject. In context of the present invention, examples for such bone disorders are osteoporosis, osteopenia, bone fracture, impaired bone homeostasis or. Examples for such cardiovascular disorders are cardiovascular diseases such as stroke, infarction, hypertension, thrombosis, vascular stenosis, coronary syndromes, vascular dementia, heart failure and renal failure, as well as atherosclerosis (Erusalimsky, J Appl Physiol (2009), 106: 326-32). As described in the appended examples, it could also surprisingly be shown that miR-31 is specifically elevated in stress-induced senescent endothelial cells as well as exosomes of stress-induced premature senescent endothelial cells. Accordingly, an antagonist/inhibitor of miR-31 is also to be used in context of this invention for the medical intervention of stress-related cardiovascular disorders, like cardiovascular disorders due to oxidative stress or hypoxia/reperfusion damage.

In accordance with the above and the experimental data provided herein, the present invention relates to a composition comprising an antagonist/inhibitor of a polynucleotide that is capable of decreasing or suppressing expression of FZD3 or a biologically active derivative thereof and/or an antagonist/inhibitor of miR-31 or its 5' or 3' isoforms or variants for use in treating or preventing bone disorders and/or cardiovascular disorders in a subject. Preferably, said subject is a human subject. Also provided is a method for treating or preventing bone disorders and/or cardiovascular disorders in a subject, said method comprising administering an effective amount of a composition comprising an antagonist/inhibitor of a polynucleotide that is capable of decreasing or suppressing expression of FZD3 or a biologically active derivative thereof and/or administering an effective amount of a composition comprising an antagonist/inhibitor of miR-31 or its 5' or 3' isoforms or variants. Again, also in this method of treatment the most preferred subject to be treated is a human subject in need of medical intervention.

In context of the present invention, it has surprisingly been found how the senescent secretome and especially senescent cell derived exosomes influence adult stem cells and, thus, tissue regeneration. For this purpose, the present inventors investigated two prime characteristics of such stem cells: self renewal/cell division as well as differentiation potential. As models for investigating a possible effect of the senescent endothelial secretome on adult stem cells, adipose-tissue derived stem cells (ASCs) were selected.

Furthermore, in context of the present invention it was surprisingly found that senescent endothelial cells secrete miRNAs packaged into exosomes, that these vesicles are taken up by target cells suggesting a paracrine signalling function and that the amount of specific miRNAs differs in young versus senescent endothelial cells in vitro. As has been found in context of the present invention, a microRNA (miRNA), miR-31, is markedly increased in the supernatant of senescent cells, protected and transported by exosomes, as well as in the blood of a subgroup of elderly donors. Furthermore, in context of the present invention, it has been found that miR-31 is taken up by ASCs by exposing them to supernatant or purified exosomes of senescent endothelial cells as well as by exposure to blood-derived exosomes of elderly individuals.

In context with the present invention, the target of miR-31 that is responsible for osteogenic inhibition was identified as frizzled-3 (FZD3), which so far has only been described as important for the development of the neuronal system since FZD3 knock-out mice show defects in aconal growth and guidance (Endo, Mol Cell Biol (2008), 28: 2368-2379; Stuebner, Dev Dyn (2010), 239: 246-260; Wang, J Neurosci (2006), 26: 2147-2156; Wang, J Neurosci (2002), 22: 8563-8573; Wang, J Neurosci (2006), 26: 366-364). Furthermore, it has been found herein that miR-31 inhibits osteogenic differentiation and increases proliferation of ASCs. These surprising findings show that polynucleotides decreasing or suppressing expression of FZD3, like (but not limited to) miR-31, represent a novel marker of biological age or of age-associated diseases like osteoporosis, osteopenia, bone fracture or impaired bone homeostasis or cardiovascular diseases such as stroke, infarction, hypertension, thrombosis, vascular stenosis, coronary syndromes, vascular dementia, heart failure and renal failure or atherosclerosis and the like. Furthermore, antagonists/inhibitors of polynucleotides that decrease or suppress the expression of FZD3, like antagonists/inhibitors of miR-31 and/or of miR-31 or its 5' or 3' isoforms or variants represents novel therapeutics. Accordingly, in particular miR-31 and/or of miR-31 or its 5' or 3' isoforms or variants represent novel therapeutic targets in all diseases that require osteogenesis and bone formation, such as osteoporosis, osteopenia, bone fracture, impaired bone homeostasis, bone cancer, etc. as well as in cardiovascular diseases such as stroke, infarction, hypertension, thrombosis, vascular stenosis, coronary syndromes, vascular dementia, heart and renal failure or atherosclerosis. Examples of 3' and 5' isoforms of miR-31 are shown in Table 3.

In context of the present invention, the functionality of miR-31 delivery was tested on the proliferation and differentiation capacity of ASCs. As has been found in context of the present invention, the cell numbers reached within a batch were higher, while osteogenic differentiation was partially inhibited by senescent exosomes or miR-31 alone.

Furthermore, in context of the present invention it was surprisingly found that miR-31 is upregulated significantly in sera of elderly donors. This shows that exosomal delivery of miR-31 is also found in the blood and not only in vitro during cellular senescence. Furthermore, in context of the present invention, using elderly blood-derived exosomes, inhibition of osteogenesis was again observed. So far, miR-31 was not described to be present in serum derived exosomes. Accordingly, in context of the present invention, miR-31 is a valuable tool as a biomarker for aging and age-associated such as osteoporosis, osteopenia, bone fracture or impaired bone homeostasis or cardiovascular diseases such as stroke, infarction, hypertension, thrombosis, vascular stenosis, coronary syndromes, vascular dementia, heart and renal failure or atherosclerosis.

Additionally, in context of the present invention, besides the upregulation of miR-31 in elderly subjects, miR-31 was found to be elevated in a first set of experiments in 2 out of 4 osteopenia patients. In more detailed experiments as provided in the enclosed examples, 7 out of 10 osteopenia patients either show a stable disease or progression to osteoporosis where miR-31 was found in blood serum. Furthermore, as shown in the appended examples, inhibition of miR-31 improves osteogenic differentiation, while transient increase of miR-31 results in decreased osteogenic differentiation. This finding demonstrates that inhibition of miR-31 improves osteoblast formation. This is very useful in the medical invention of bone disorders, e.g., osteoporosis. Furthermore, expression of miR-31 is indicative for such bone disorders (and also for cardiovascular disorders). Therefore, specific assays for the detection of miR-31 are also provided herein. Such detection assays are preferably carried out on biological samples, like serum and blood plasma and the like. Osteoporosis is defined as a disease characterized by low bone mass and structural deterioration of bone tissue, leading to bone fragility and an increased susceptibility to fractures. Osteoporosis is an age-related systemic condition that naturally occurs among mammals, mainly in humans (Xu, Endocr Rev (2010), 31(4): 447-505). Accordingly, the present invention also provides for a good and reliable biomarker for bone disorders, like osteoporosis and/or osteopenia. The biomarker provided herein is also useful in the diagnosis of cardiovascular disorders. The appended examples also show that miR-31 is elevated in stress-induced senescent endothelial cells. Furthermore, as shown herein, miR-31 is elevated in exosomes of stress-induced premature senescent endothelial cells. Accordingly, miR-31 is also indicative for cardiovascular disorders.

Generally, in accordance with the present invention, when referring to a polynucleotide to be inhibited in context of the present invention, said polynucleotide is capable of decreasing or suppressing expression of FZD3 or a biologically active derivative thereof as described and exemplified in detail herein.

As could be demonstrated in the present invention, the expression of FZD3 can be decreased or suppressed by polynucleotides described herein contained in senescent exosomes, e.g., by hybridizing to the mRNA of FZD3. Thereby, for instance, degradation of or prevention of translation of FZD3 mRNA can be induced, both resulting in suppression or decreasing of expression of FZD3. Accordingly, inhibition of the polynucleotides described herein which inhibit or suppress expression of FZD3 would increase of expression of FZD3. In context of the present invention, ASCs undergoing osteogenic differentiation were tested for FZD3 transcription. Indeed, it was upregulated after 4 days compared to cells treated with control medium (FIG. 7A). Moreover, FZD3 levels were significantly downregulated after treatment with senescent exosomes compared to treatment with young exosomes and control treated cells (FIG. 7B). 24 h after miR-31 transfection, FDZ3 was also downregulated, but did not reach significant levels, which might be explained due to the very low mRNA levels of FDZ3 when cells are not differentiating (FIG. 7C). Thus, FZD3 represents not only a marker but also a necessary factor for osteogenic differentiation and turns out to be a direct target of polynucleotides to be inhibited in context of the present invention also in ASCs.

As described and exemplified in the present invention, inhibition of the polynucleotides to be inhibited in context of the present invention is particularly useful in the treatment or prevention of osteoporosis, osteopenia, bone fracture or impaired bone homeostasis or cardiovascular diseases such as stroke, infarction, hypertension, thrombosis, vascular stenosis, coronary syndromes, vascular dementia, heart and renal failure or atherosclerosis in a subject.

DETAILED DESCRIPTION OF THE INVENTION

In one embodiment of the present invention, the polynucleotide to be inhibited in context of the present invention, i.e. which is capable of decreasing or suppressing expression of FZD3 or a biologically active derivative thereof (such as miR-31), may be a microRNA (also abbreviated herein as miRNA or miR) or a precursor thereof, a mimic microRNA or a precursor thereof, an siRNA or a precursor thereof, a long non-coding RNA or a precursor thereof, an snRNA (small/short hairpin RNA) or a precursor thereof, an stRNA (small temporal RNA) or a precursor thereof, an fRNA (functional RNA) or a precursor thereof, an snRNA (small nuclear RNA) or a precursor thereof, a snoRNA (small nucleolar RNA) or a precursor thereof, a piRNA (piwi-interacting RNA) or a precursor thereof, a tasiRNA (trans-acting small/short interfering RNA) or a precursor thereof, an aRNA (antisense RNA) or a precursor thereof, or a small non-coding RNA or a precursor thereof. In accordance with the present invention, as artificial polynucleotides mentioned hereinabove may have the same effect on the expression of FZD3 or biologically active derivatives thereof (i.e. decreasing or suppressing said expression) as physiological polynucleotides mentioned hereinabove, inhibitors of such artificial polynucleotides may at the same time also be inhibitors of such physiological polynucleotides. As used herein, "precursors" of a polynucleotide to be inhibited in context of the present invention, i.e. which is capable of decreasing or suppressing expression of FZD3 or a biologically active derivative thereof, may be forms of the respective polynucleotides as they occur during maturation of the respective polynucleotides. For example, in context of the present invention, precursors of a microRNA or a mimic microRNA may be primary miRNAs (pri-miRNAs) or precursor miRNAs (pre-miRNAs) as occurring during maturation of miRNAs. Both are single transcripts (i.e. ssRNA) that fold into a characteristic intramolecular secondary structure, the so-called "hairpin loop", which contains a stretch of about 18 to 23 base pairs, which may be interrupted by mismatches. In context of the present invention, precursors of siRNAs may be long dsRNA molecules or shorter "hairpin loop" ssRNA molecules. Both types of these siRNA precursors may contain a stretch of base pairs without any mismatch. The current model for maturation of mammalian miRNAs is nuclear cleavage of the primary miRNA (pri-miRNA) which liberates a 60-70 nt stem loop intermediate, known as the direct miRNA precursor or pre-miRNA. The mature about 18-23 nt long miRNA is yielded from one arm of the stem loop precursor (Bartel, Cell (2004), 116: 281-297; Lee, EMBO J (2002), 21: 4663-4670; Zeng and Cullen, RNA (2003), 9: 112-123). In a preferred embodiment of the present invention, the polynucleotide to be inhibited in accordance with the present invention is a microRNA or a precursor thereof or a mimic microRNA or a precursor thereof. The polynucleotides described in and to inhibited in context of the present invention may be of any length. Preferably, the polynucleotide is about 15 to about 100 nucleotides in length, more preferably about 18 to about 27 nucleotides and most preferably about 20 to about 24 nucleotides.

In a specific embodiment of the present invention, the polynucleotide to be antagonized/inhibited in context of the present invention, i.e. the polynucleotide being capable of decreasing or suppressing expression of FZD3 or a biologically active derivative thereof and/or the miR-31 miR-31 or its 5' or 3' isoforms or variants to be antagonized/inhibited, may be selected from the group consisting of:
    (a) a polynucleotide comprising the nucleotide sequence of SEQ ID NO: 1 (i.e. miR-31);
    (b) a polynucleotide which is at least 80% identical to the polynucleotide of (a);
    (c) a polynucleotide comprising the nucleotide sequence of SEQ ID NO: 2 (i.e. the seed sequence of miR-31: GGCAAGAU); and (d) a polynucleotide according to (b) comprising the nucleotide sequence of SEQ ID NO: 2 (i.e. the seed sequence of miR-31: GGCAAGAU).

According to the present invention, identity levels of polynucleotides refer to the entire length of the nucleotide sequence of the referred to SEQ ID NOs. and is assessed pair-wise, wherein each gap is to be counted as one mismatch. For example, the term "identity" may be used herein in the context of a polynucleotide to be inhibited in context of the present invention which has a nucleic acid sequence with an identity of at least 80%, 85%, 90%, 95%, 97%, 98% or 99% to a polynucleotide comprising or consisting of the nucleotide sequence of any one of SEQ ID NO: 1 (mature miR-31), SEQ ID NO: 2 (seed sequence of miR-31), or SEQ ID NO: 3 (pre-miR-31) as also shown in Table 1 herein, preferably over the entire length. Furthermore, in the context of the present invention, a polynucleotide to be inhibited in context of the present invention may also have a nucleic acid sequence with an identity of at least 80%, 85%, 90%, 95%, 97%, 98% or 99% to a polynucleotide comprising or consisting of a nucleotide sequence consisting of the sequence of SEQ ID NO: 1 or SEQ ID NO: 3 as shown in Table 1 herein including one, two or more nucleotide(s) of the corresponding mature- or pre-miRNA sequence at the 5'-end and/or the 3'-end of the respective seed sequence. For example, in the context of the present invention, a polynucleotide to be inhibited in context of the present invention may have a nucleic acid sequence with an identity of at least 80%, 85%, 90%, 95%, 97%, 98% or 99% to a polynucleotide comprising or consisting of the nucleotide sequence AGGCAAGAUGC (i.e. the seed sequence of SEQ ID NO: 1 including one nucleotide of the corresponding mature sequence at the 5'-end and one nucleotide of the corresponding mature sequence at the 3'-end). If two nucleic acid sequences being compared by sequence comparisons differ in identity, then the term "identity" refers to the shorter sequence and to the part of the longer sequence that matches said shorter sequence. Therefore, when the sequences which are compared do not have the same length, the degree of identity preferably either refers to the percentage of nucleotide residues in the shorter sequence which are identical to consecutive nucleotide residues contained in the longer sequence or to the percentage of consecutive nucleotides contained in the longer sequence which are identical to the nucleotide sequence of the shorter sequence. Of course, as described above, a gap as "part of consecutive nucleotides" is to be counted as a mismatch. In this context, the skilled person is readily in the position to determine that part of a longer sequence that "matches" the shorter sequence. Also, these definitions for sequence comparisons (e.g., establishment of "identity" values) are to be applied for all sequences described and disclosed herein.

TABLE 1 miRNAs, miRBase ID (miRBase: http://www.mirbase.org, version number 15: released April 2010), and mature and pre-miR sequences (seed sequences underscored).

| miRNA | miRBase ID | Sequence | SEQ ID NO. |
|---|---|---|---|
| mature miR-31 | MI0000089 | A<u>GGCAAGAU</u>GCUGGCAUAGCU | 1 |
| seed miR-31 | MI0000089 | <u>GGCAAGAU</u> | 2 |

TABLE 1-continued miRNAs, miRBase ID (miRBase: http://www.mirbase.org, version number 15: released April 2010), and mature and pre-miR sequences (seed sequences underscored).

| miRNA | miRBase ID | Sequence | SEQ ID NO. |
|---|---|---|---|
| pre-miR-31 | MI0000089 | GGAGAGGA<u>GGCAAGAU</u>GCUGG CAUAGCUGUUGAACUGGGAAC CUGCUAUGCCAACAUAUUGCCA UCUUUCC | 3 |

TABLE 2

Examples for nucleic acid molecules that a capable of hybridizing to the above identified miRNAs, seed sequences and the like.

| miRNA | Hybidizing Sequence | SEQ ID NO. |
|---|---|---|
| mature miR-31 | AGCUAUGCCAGCAUCUUGCCU | 6 |
| seed miR-31 | AUCUUGCC | 7 |
| pre-miR-31 | GGAAAGAUGGCAAUAUGUUGGCAUAG CAGGUUCCCAGUUCAACAGCUAUGCC AGCAUCUUGCCUCCUCUCC | 8 |

As used herein, thymine (T) and uracil (U) may be used interchangeably depending on the respective type of polynucleotide.

Such hybridizing sequences (or functional fragments or isoforms thereof) may be employed as specific antagonists/inhibitors polynucleotide that is capable of decreasing or suppressing expression of FZD3 or a biologically active derivative thereof, and/or as specific antagonists/inhibitors an antagonist/inhibitor of miR-31 or its 5' or 3' isoforms or variants. Such hybridizing sequences (or functional fragments or isoforms thereof) may hybridize to all kinds of polynucleotides to be antagonized or inhibited as described herein, including microRNAs, siRNAs, mimic microRNAs, long non-coding RNAs, snRNAs, stRNAs, (RNAs, snRNAs, snoRNAs, piRNAs, tasiRNAs, aRNAs as well as precursors of such RNAs.

TABLE 3

Examples of 5' and 3' isoforms of miR-31

| 5'-isoform | SEQ ID NO. | 3'-isoform | SEQ ID NO. |
|---|---|---|---|
| GAGGCAAGAUGCUGGCAUAGCU | 9 | UGCUAUGCCAACAUAUUGCCAUC | 23 |
| AGGCAAGAUGCUGGCAUAGCUG | 10 | UGCUAUGCCAACAUAUUGCCAU | 24 |
| AGGCAAGAUGCUGGCAUAGCUGU | 11 | UGCUAUGCCAACAUAUUGCCA | 25 |
| AGGCAAGAUGCUGGCAUAGCU | 12 | UGCUAUGCCAACAUAUUGCCAUCU | 26 |
| AGGCAAGAUGCUGGCAUAG | 13 | GCUAUGCCAACAUAUUGCCAUC | 27 |
| AGGCAAGAUGCUGGCAUAG | 14 | CUAUGCCAACAUAUUGCCAUC | 28 |
| AGGCAAGAUGCUGGCAUAGCUGUU | 15 | | |

TABLE 3-continued

Examples of 5' and 3' isoforms of miR-31

| 5'-isoform | SEQ ID NO. | 3'-isoform | SEQ ID NO. |
|---|---|---|---|
| AGGCAAGAUGCUGGCAU | 16 | | |
| AGGCAAGAUGCUGGCAUA | 17 | | |
| AGGCAAGAUGCUGGCA | 18 | | |
| GGCAAGAUGCUGGCAUAGCUG | 19 | | |
| GGCAAGAUGCUGGCAUAGCU | 20 | | |
| GGCAAGAUGCUGGCAUAGCUGUU | 21 | | |
| GGCAAGAUGCUGGCAUAGCUGU | 22 | | |

As used herein, thymine (T) and uracil (U) may be used interchangeably depending on the respectivetype of polynucleotide.

Identity, moreover, means that there is preferably a functional and/or structural equivalence between the corresponding nucleotide sequences. Nucleic acid sequences having the given identity levels to the particular nucleic acid sequences of the polynucleotides to be inhibited in context of the present invention may represent derivatives/variants of these sequences which, preferably, have the same biological function. In context of the present invention, the biological function of a polynucleotide to be inhibited in context of the present invention is the ability to decrease or suppress expression of FZD3 or a biologically active derivative thereof, e.g., by hybridizing to the mRNA of FZD3, thereby inducing degradation or preventing translation of the FZD3 mRNA. Whether the expression of FZD3 or a biologically active derivative thereof has been decreased or suppressed can be easily tested by methods well known in the art and as also described herein. Examples of such methods suitable to determine whether the expression of FZD3 or a biologically active derivative is decreased or suppressed are polyacrylamide gel electrophoresis and related blotting techniques such as Western Blot paired with chromogenic dye-based protein detection techniques (such as silver or coomassie blue staining) or with fluorescence- and luminescence-based detection methods for proteins in solutions and on gels, blots and microarrays, such as immunostaining, as well as immunoprecipitation, ELISA, microarrays, and mass spectrometry. To determine whether a given polynucleotide hybridizes to the mRNA of FZD3 can also be tested by methods well known in the art and as also described herein. Examples of such methods suitable to determine whether a given polynucleotide hybridizes to another nucleic acid (e.g., the mRNA of FZD3 or a biologically active derivative thereof) are reporter gene assays in which commonly used reporter genes are fluorescent proteins such as GFP, eGFP, YFP, eYFP, BFP, eBFP, luminescent proteins such as the enzymes Renilla or firefly luciferase, and β-galactosidase encoded by the lacZ gene (Inui, Nat Rev Mol Cell Biol (2010), 11: 252-63). Whether the mRNA of FZD3 is degraded or its translation is prevented can also be tested by methods known in the art and as also described herein. Examples for methods suitable to determine whether an mRNA is degraded are qPCR, RT-PCR, qRT-PCR, RT-qPCR, Light Cycler®, TaqMan® Platform and Assays or quantigene assay (Zhou, Anal Biochem (2000), 282: 46-53) Northern blot, dot blot, RNAse protection assays, microarrays, next generation sequencing (VanGuilder, Biotechniques (2008), 44(5): 619-26; Elvidge, Pharmacogenomics (2006), 7: 123-134; Metzker, Nat Rev Genet (2010), 11: 31-46; Kafatos, NAR (1979), 7: 1541-1552).

The polynucleotides described herein, e.g. those to be inhibited in context of the present invention may be either naturally occurring variations, for instance sequences from other varieties, species, etc., or mutations, and said mutations may have formed naturally or may have been produced by deliberate mutagenesis. Furthermore, the variations may be synthetically produced sequences. The allelic variants may be naturally occurring variants or synthetically produced variants or variants produced by recombinant DNA, RNA, PNA, GNA, TNA or LNA techniques known in the art. Deviations from the above-described nucleic acid sequences may have been produced, e.g., by deletion, substitution, addition, insertion of nucleotides and/or by recombination. The term "addition" refers to adding at least one nucleic acid residue to one or both ends of the given sequence, whereas "insertion" refers to inserting at least one nucleic acid residue within a given nucleotide sequence. The term "deletion" refers to deleting or removal of at least one nucleic acid residue in a given nucleotide sequence. The term "substitution" refers to the replacement of at least one nucleic acid residue in a given nucleotide sequence. The definitions for polynucleotides to be inhibited above and below apply mutatis mutandis for all nucleic acid molecules and polynucleotides provided and described herein including those acting as an antagonist/inhibitor.

The polynucleotides described herein, e.g., those to be inhibited in context of the present invention (i.e. polynucleotides which decreases or suppresses expression of FZD3) or those acting as antagonists/inhibitors, may be nucleic acid analogues such as DNA molecules, RNA molecules, oligonucleotide thiophosphates, substituted ribo-oligonucleotides, LNA molecules, PNA molecules, GNA (glycol nucleic acid) molecules, TNA (threose nucleic acid) molecules, morpholino polynucleotides, or antagomir (cholesterol-conjugated; for antagonists/inhibitors) polynucleotides. Furthermore, in context of the present invention, the term "polynucleotide" as well as the term "nucleic acid molecule" may refer to nucleic acid analogues such as DNA molecules, RNA molecules, oligonucleotide thiophosphates, substituted ribo-oligonucleotides, LNA molecules, PNA molecules, GNA (glycol nucleic acid) molecules, TNA (threose nucleic acid) molecules, morpholino polynucleotides, or antagomir (cholesterol-conjugated; for antagonists/inhibitors) polynucleotides or hybrids thereof or any modification thereof as known in the art (see, e.g., U.S. Pat. No. 5,525,711, U.S. Pat. No. 4,711,955, U.S. Pat. No. 5,792,608 or EP 302175 for examples of modifications). Nucleic acid residues comprised by the polynucleotides may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). In context of the present invention, thymine (T) and uracil (U) may be used interchangeably depending on the respective type of polynucleotide. For example, as the skilled person is aware of, a thymine (T) as part of a DNA corresponds to an uracil (U) as part of the corresponding transcribed mRNA. The polynucleotides may be single- or double-stranded, linear or circular, natural or synthetic, and, if not indicated otherwise, without any size limitation. For instance, the polynucleotide to be inhibited in context of the present invention may be a microRNA (miRNA) or a precursor thereof, a mimic microRNA or a precursor thereof, an siRNA or a precursor thereof, a long non-coding RNA or a precursor thereof, an snRNA (small/short hairpin RNA) or a precursor thereof, an stRNA (small temporal RNA) or a precursor thereof, an fRNA (functional RNA) or a precursor thereof, an snRNA (small nuclear RNA) or a precursor thereof, a snoRNA (small nucleolar RNA) or a precursor thereof, a piRNA (piwi-interacting RNA) or a precursor thereof, a tasiRNA (trans-acting small/short interfering RNA) or a precursor thereof, an aRNA (antisense RNA) or a precursor thereof, or a small non-coding RNA or a precursor thereof, genomic DNA, cDNA, mRNA, ribozymal or a DNA encoding the before mentioned RNAs or chimeroplasts (Gamper, Nucleic Acids Research (2000), 28, 4332-4339). As already described, as used herein, "precursors" of the polynucleotides to be inhibited in context of the present invention may be forms of the respective polynucleotides as they occur during maturation of the respective polynucleotides. For example, in context of the present invention, precursors of a microRNA or a mimic microRNA may be primary miRNAs (pri-miRNAs) or precursor miRNAs (pre-miRNAs) as occurring during maturation of miRNAs. Both are single transcripts (i.e. ssRNA) that fold into a characteristic intramolecular secondary structure, the so-called "hairpin loop", which contains a stretch of about 18 to 23 base pairs, which is often interrupted by mismatches. In context of the present invention, precursors of siRNAs may be long dsRNA molecules or shorter "hairpin loop" ssRNA molecules. Both types of these siRNA precursors may contain a stretch of base pairs without any mismatch. The current model for maturation of mammalian miRNAs is nuclear cleavage of the primary miRNA (pri-miRNA) which liberates a 60-70 nt stem loop intermediate, known as the miRNA precursor or pre-miRNA. The mature about 18-23 nt long miRNA is yielded from one arm of the stem loop precursor (Bartel, Cell (2004), 116: 281-297; Lee, EMBO J (2002), 21: 4663-4670; Zeng and Cullen, RNA (2003), 9: 112-123). Said polynucleotides may be in the form of a plasmid or of viral DNA or RNA. Preferably, the polynucleotide to be inhibited in context of the present invention is a microRNA or a mimic microRNA.

In one embodiment, the polynucleotide to be inhibited in context of the present invention comprises or consists of the nucleotide sequence of any one of SEQ ID NO: 1 (mature miR-31), SEQ ID NO: 2 (seed sequence of miR-31), or SEQ ID NO: 3 (pre-miR-31) as also shown in Table 1 herein. Furthermore, a polynucleotide to be inhibited in context of the present invention may also have a nucleic acid sequence comprising or consisting of a nucleotide sequence consisting of the seed sequence of SEQ ID NO: 1 or SEQ ID NO: 3 as shown in Table 1 including one, two, three or more nucleotide(s) of the corresponding mature- or pre-miR sequence at the 5'-end and/or the 3'-end of the respective seed sequence. For example, a polynucleotide to be inhibited in context of the present invention may have a nucleic acid sequence comprising or consisting of the nucleotide sequence [A] G-G-C-A-A-G-A-U [GC] (i.e. the seed sequence of SEQ ID NO: 1 plus one nucleotide of the corresponding mature miRNA sequence at the 5'-end and two nucleotides of the corresponding mature miRNA sequence at the 3'-end) or [A] G-G-C-A-A-G-A-U [G] (i.e. the seed sequence of SEQ ID NO: 1 plus one nucleotide of the corresponding mature sequence at the 5'-end and one nucleotide of the corresponding mature sequence at the 3'-end). Polynucleotides to be inhibited in context of the present invention (i.e. polynucleotides which decrease or suppress expression of FZD3) may also comprise or consist of the nucleotide sequence shown in any one of SEQ ID NO: 1 (mature miR-31), SEQ ID NO: 2 (seed sequence of miR-31), or SEQ ID NO: 3 (pre-miR-31) as also shown in Table 1 herein, wherein one, two, three, four, five or more nucleotides are added, deleted or substituted. Furthermore, a polynucleotide to be inhibited in context of the present invention may also have a nucleic acid sequence comprising or consisting of the nucleotide a nucleotide sequence consisting of the seed sequence of SEQ ID NO: 1 or SEQ ID NO: 3 as shown in Table 1 including one, two, three or more nucleotide(s) of the corresponding mature- or pre-miR sequence at the 5'-end and/or the 3'-end of the respective seed sequence, wherein one, two, three, four, five or more nucleotides are added, deleted or substituted. For example, a polynucleotide to be inhibited in context of the present invention may have a nucleic acid sequence comprising or consisting of the nucleotide sequence [A] G-G-C-A-A-G-A-U [U] (i.e. the seed sequence of SEQ ID NO: 1 plus one nucleotide of the corresponding mature sequence at the 5'-end and one nucleotide of the corresponding mature sequence at the 3'-end, wherein the nucleotide at the 3'-end has been substituted by U). Preferably, said addition, deletion or substitution of one, two, three, four, five or more nucleotides is not effected within the seed sequence of a polynucleotide as shown in Table 1 herein. Also, the polynucleotide to be inhibited in context of the present invention may comprise or consist of a polynucleotide being at least 80%, 85%, 90%, 95%, 97%, 98% or 99% identical to a polynucleotide comprising or consisting of the nucleotide sequence of any one of SEQ ID NO: 1 (mature miR-31), SEQ ID NO: 2 (seed sequence of miR-31) or SEQ ID NO: 3 (pre-miR-31) as also shown in Table 1 herein. Furthermore, a polynucleotide to be inhibited in context of the present invention may also comprise or consist of a nucleic acid sequence with an identity of at least 80%, 85%, 90%, 95%, 97%, 98% or 99% to a polynucleotide comprising or consisting of a nucleotide sequence consisting of the seed sequence of SEQ ID NO: 1 or SEQ ID NO: 3 as shown in Table 1 including one, two or more nucleotide(s) of the corresponding mature- or pre-miR sequence at the 5'-end and/or the 3'-end of the respective seed sequence. For example, a polynucleotide to be inhibited in context of the present invention may comprise or consist of a nucleic acid sequence with an identity of at least 80%, 85%, 90%, 95%, 97%, 98% or 99% to a polynucleotide comprising or consisting of the nucleotide sequence G-G-C-A-A-G-A-U [GC] (i.e. the seed sequence of SEQ ID NO: 1 plus two nucleotides of the corresponding mature sequence at the 3'-end). Additionally, a polynucleotide to be inhibited in context of the present invention may also comprise or consist of a nucleic acid sequence with an identity of at least 80%, 85%, 90%, 95%, 97%, 98% or 99% to a polynucleotide comprising or consisting of the nucleotide sequence of any one of SEQ ID NO: 1 (mature miR-31) or SEQ ID NO: 3 (pre-miR-31) as also shown in Table 1 herein and comprise the nucleic acid sequence as shown in SEQ ID NO: 2 (seed sequence of miR-31) as shown in Table 1 herein.

Generally, as used herein, a polynucleotide comprising the nucleic acid sequence of a sequence provided herein may also be a polynucleotide consisting of said nucleic acid sequence. In one embodiment, the polynucleotide to be inhibited in context of the present invention has the nucleic acid sequence as shown in SEQ ID NO: 1.

In context of the determination whether two given nucleic acid molecules are able to hybridize, e.g., whether a polynucleotide to be inhibited in context of the present invention hybridizes to an mRNA of FZD3 or a biologically active derivative thereof, or whether an inhibitor described in and used in accordance with the present invention hybridizes to a polynucleotide to be inhibited in context of the present invention, the hybridization may occur and be detected under physiological or artificial conditions, under stringent or non-stringent conditions. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known in the art, the length of the probe and the composition of the nucleic acid to be determined constitute further parameters of the hybridization conditions. Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. In accordance to the invention described herein, low stringent hybridization conditions for the detection of homologous or not exactly complementary sequences may, for example, be set at 6×SSC, 1% SDS at 65° C. As is well known in the art, the length of the probe and the composition of the nucleic acid to be determined constitute further parameters of the hybridization conditions. Polynucleotides to be inhibited in context of the present invention which hybridize to the mRNA of FZD3 or a biologically active derivative thereof also comprise fragments of the above described polynucleotides which are to be inhibited in context of the present invention. Such fragments preferably are polynucleotides which are able to decrease or suppress expression of FZD3 or a biologically active derivative thereof. Such fragments may be, e.g., polynucleotides such as siRNAs or siRNA pools consisting of 4 siRNAs targeting the mRNA of FZD3 as can be purchased from Dharmacon (on-target plus smart-pool L-005502-00-0005, NM_017412). Furthermore, a hybridization complex refers to a complex between two nucleic acid sequences by virtue of the formation of hydrogen bonds between complementary G and C bases and between complementary A and T (or U, respectively) bases; these hydrogen bonds may be further stabilized by base stacking interactions. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T (or U, respectively)" binds to the complementary sequence "T (or U, respectively)-C-A". Complementarity between two single-stranded molecules may be "partial", in which only some of the bases of the nucleic acids bind, or it may be complete when total complementarity exists between single-stranded molecules. The degree of complementarity between nucleic acid strands has significant effects on the efficiency and strength of hybridization between nucleic acid strands.

In order to determine whether two nucleic acid molecules hybridize, e.g., whether a given polynucleotide hybridizes to the mRNA of FZD3 or a biologically active derivative thereof as described herein, thereby inducing degradation or preventing translation of said mRNA of FZD3 or a biologically active derivative thereof, or whether an inhibitor described in and used in accordance with the present invention hybridizes to a polynucleotide to be inhibited in context of the present invention, various tests known in the art and also described herein may be applied. In this context, the hybridization may occur and be tested under physiological conditions or under artificial conditions as known in the art and also described herein. For example, a test to determine hybridization between an miRNA and an mRNA may be a Luciferase Assay as also described herein and in technical bulletins by Promega (C8021 (psiCHECK-2 Vector), E1960 (Dual-Luciferase® Reporter Assay System)). In context of the present invention, general examples of methods suitable to determine whether a polynucleotide hybridizes to another nucleic acid (e.g., the 3'UTR of the mRNA of FZD3) are reporter gene assays in which common reporter genes are used such as fluorescent proteins (e.g., GFP, eGFP, YFP, eYFP, BFP, or eBFP), or luminescent proteins (e.g., Renilla or firefly luciferase, or 3-galactosidase encoded by the lacZ gene). Furthermore, degradation of mRNA or the level of the respective translation product (to test whether the translation of the mRNA was decreased or prevented) can easily be examined by methods known in the art. Examples for methods suitable to examine degradation or stabilization of mRNA are qPCR, RT-PCR, qRT-PCR, RT-qPCR, Light Cycler®, TaqMan® Platform and Assays, Northern blot, dot blot, microarrays, next generation sequencing (VanGuilder, Biotechniques (2008), 44: 619-26; Elvidge, Pharmacogenomics (2006), 7: 123-134; Metzker, Nat Rev Genet (2010), 11: 31-46). Examples for methods suitable to examine whether the translation of a mRNA has been prevented or decreased are polyacrylamide gel electrophoresis and related blotting techniques such as Western Blot paired with chromogenic dye-based protein detection techniques (such as silver or coomassie blue staining) or with fluorescence- and luminescence-based detection methods for proteins in solutions and on gels, blots and microarrays, such as immunostaining, as well as immunoprecipitation, ELISA, microarrays, and mass spectrometry (Western Blot (Burnette, Anal Biochem (1981) 112: 195-203) or ELISA (Crowther, JA. The ELISA Guidebook. Humana Press; Totowa, N.J.: 2001).

In context of the present invention, in order to determine whether a given polynucleotide decreases or suppresses expression of FZD3 or a biologically active derivative thereof (e.g., by hybridizing to the mRNA of FZD3 and thereby inducing degradation or preventing translation of FZD3 mRNA), the level of expressed FZD3 can be easily detected. In context of the present invention, a polynucleotide is to be assessed as decreasing or suppressing expression of FZD3 or a biologically active derivative thereof if the detected level of expressed FZD3 in a test sample which was contacted with a polynucleotide to be tested is at least 1.5 fold, preferably at least L75 fold, more preferably at least 2.0 fold, and most preferably at least 2.5 fold lower than the FZD3 expression level of a control sample which was not contacted with the polynucleotide. For example, a Western blot analysis can be performed for FZD3 protein detection.

Furthermore, in one embodiment, the polynucleotides to be inhibited in context of the present invention may hybridize to the 3'UTR (untranslated region) of the mRNA of FZD3 or a biologically active derivative thereof or to fragments of said 3'UTR. Hybridization between a polynucleotide to be inhibited in context of the present invention and the 3'UTR of the mRNA of FZD3 or a biologically active derivative thereof can easily be tested as described hereinabove. Preferably, by hybridizing to the 3'UTR of the mRNA of FZD3 or a biologically active derivative thereof or to fragments of said 3'UTR, the polynucleotide to be inhibited in context of the present invention induces degradation of or prevents translation of said mRNA of FZD3 or a biologically derivative thereof. Generally, in context of the present invention, when referring to FZD3, reference is made to GenBank Accession No. NM_017412, Version No. 177 (released on Apr. 15, 2010). The sequence of the 3'UTR of FZD3 mRNA is shown in SEQ ID NO: 4 herein. In one embodiment, the polynucleotide to be inhibited in context of the present invention is able to hybridize to a nucleic acid sequence comprising nucleotides 3419-3426 of SEQ ID NO: 4, preferably thereby inducing degradation of or prevention of translation of the mRNA of FZD3 or a biologically derivative thereof.

The polynucleotide to be inhibited in context of the present invention may be comprised in lipid composition, an exosome, a vesicular body, a liposome, in PEI (polyethylene imine) or atellocollagen. Also, in accordance with the present invention, the antagonist/inhibitor of a polynucleotide to be inhibited (i.e. that is capable of decreasing or suppressing expression of FZD3 or a biologically derivative thereof) may be comprised in a lipid composition, an exosome or a liposome. For example, an antagonist/inhibitor may be an antagonist/inhibitor of miR-31 or its 3' or 5' isoforms or variants as described herein. Examples for 3' and 5' isoforms of miR-31 are shown in Table 3. The present invention also relates to such lipid compositions, exosomes and liposomes for use in the medical interventions described herein, e.g., for use in treating or preventing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject.

As used herein, a biologically active derivative of FZD3 means that is has the same biological function as FZD3, i.e. it is able to transduce signals via the PI3K-AKT pathway (Kawasaki, Cell Signal (2007), 19: 2498-506). In context of the present invention, in order to validate whether a given compound is a biologically derivative of FDZ3, the phosphorylation status of its downstream target AKT can be tested. For this purpose, ASCs, bone marrow derived stem cells, or any other cell type that has the ability to undergo osteogenic differentiation, may be treated with compounds to be tested for FZD3-activity for different times and with different doses, or the cells may be transfected with plasmids coding for compounds to be tested for FZD3-activity. Then, cell lysates may be prepared by methods known in the art. This can be done, for example, by using cell lysis buffer (20 mM Tris-HCl (pH 7.5)), 12 mM ß-glycerophosphate, 150 mM NaCl, 5 mM EGTA, 10 mM sodium fluoride, 1% Triton X-100, 1% sodium deoxycholate, 1 mM dithiothreitol (DTT), 1 mM sodium orthovanadate, protease inhibitor cocktail (Roche, Switzerland), phosphatase inhibitor cocktail 1 and 2 (Sigma, St. Louis, Mo.). Subsequently, an analysis of phosphorylated proteins may be performed by methods known in the art, e.g., by immunoblot analyses. As an illustrative example for carrying out an immunoblot analysis, 30 µg of total proteins may be subjected to SDS-PAGE and blotted on polyvinylidene difluoride membranes (e.g., PVDF). The membranes may then be probed with anti-phospho-Akt (Ser473) antibody (Cell Signalling, Danvers, 9271) (1:500), and anti-phospho-Akt (Thr308) antibody (Cell Signalling, Danvers, 9272) (1:500). As positive control, overexpression of FZD3 can be used. As negative controls, specific PI3K inhibitors like Wortmannin or LY294002 can be used that are known to prevent AKT phosphorylation. In context of the present invention, if AKT is phosphorylated to an extent of more than 40% or more than 50% compared to untreated cell controls, the compound rested can be considered a biologically active derivative of FZD3. The nucleic acid sequence of the 3'UTR of the mRNA of a FZD3 derivative in context of the present invention may be at least 80%, 85%, 90%, 95% or 98% identical to SEQ ID NO: 4.

As already mentioned, the present invention relates to a composition comprising an inhibitor of a polynucleotide or polynucleotides to be inhibited, i.e. which are capable of decreasing or suppressing expression of FZD3 or a biologically derivative thereof for use in treating or preventing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject. The composition may also comprise an exosome and/or a liposome which contain an antagonist/inhibitor of a polynucleotide that is capable of decreasing or suppressing expression of FZD3 or a biologically derivative thereof and/or which contain an antagonist/inhibitor of miR-31 or its 3' or 5' isoforms or variants.

In accordance with the present invention, the subject to be treated or in which a bone disorder and/or cardiovascular disorder such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis is to be prevented may be mammalian. In a preferred embodiment of the present invention, the subject is human.

Generally, the composition to be used in context of the present invention may comprise an antagonist/inhibitor or exosome/liposome containing said antagonist/inhibitor which inhibits one, two, three or more of the polynucleotides to be inhibited in context of the present invention. Also, the composition may comprise two, three or more antagonists/inhibitors or exosomes/liposomes, wherein each of the antagonist/inhibitors is capable of inhibiting one, two, three or more of the polynucleotides to be inhibited in context of the present invention.

The composition described herein and to be employed in context with the present invention may contain the antagonist/inhibitor or exosome/liposome described herein in an amount of about 1 ng/kg body weight to about 100 mg/kg body weight of the subject which is to be treated or in which a bone disorder and/or cardiovascular disorder such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis is to be prevented. In a preferred embodiment of the present invention, the composition comprises the inhibitor in an amount of about 1 µg/kg body weight to about 20 mg/kg body weight, more preferably 1 mg/kg body weight to about 10 mg/kg body weight.

The composition described herein and to be employed in context of the present invention may further comprise a pharmaceutically acceptable carrier. Accordingly, the present invention also relates to a pharmaceutical composition comprising an antagonist/inhibitor of a polynucleotide or polynucleotides to be inhibited in context of the present invention, an antagonist/inhibitor of miR-31 or its 3' or 5' isoforms or variants, and/or an exosome or liposome containing said antagonist/inhibitor and further comprising a pharmaceutically acceptable carrier, excipient and/or diluent. Generally, examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, i.e. about 1 ng/kg body weight to about 100 mg/kg body weight of the subject which is to be treated or in which bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis are to be prevented. In a preferred embodiment of the present invention, the composition comprising an inhibitor of a polynucleotide or polynucleotides to be inhibited in context of the present invention comprises the inhibitor in an amount of about 1 µg/kg body weight to about 20 mg/kg body weight, more preferably 1 mg/kg body weight to about 10 mg/kg body weight. Administration of the composition may be effected or administered by different ways, e.g., enterally, orally (e.g., pill, tablet (buccal, sublingual, orally, disintegrating, capsule, thin film, liquid solution or suspension, powder, solid crystals or liquid), rectally (e.g., suppository, enema), via injection (e.g., intravenously, subcutaneously, intramuscularly, intraperitoneally, intradermally) via inhalation (e.g., intrabronchially), topically, vaginally, epicutaneously, or intranasally. In context of the present invention, compositions comprising exosomes or liposomes containing an antagonist/inhibitor of a polynucleotide capable of decreasing or suppressing expression of FZD3 or a biologically derivative thereof and/or an antagonist/inhibitor of miR-31 or its 3' or 5' isoforms or variants may be applied locally or systemically. When applied locally, e.g. directly at a defect site of a bone, the composition comprising an exosome/liposome is particularly for use in treating bone disorders such as osteoporosis, osteopenia, bone fracture or impaired bone homeostasis. Methods for applying such compositions directly to a bone are known in the art (Takeshita, Mol Ther (2010), 18: 181-187). When applied systemically (e.g., parenterally, orally or other routes described herein), said composition may be used for treating or preventing bone disorders and/or cardiovascular disorders as described herein. It is understood that also the antagonists/inhibitors described herein may be administered locally or systemically by other means, even directly. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The compositions described herein may be administered locally or systemically. Systemic administration will preferably be parenterally, e.g., intravenously. The composition may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, polyethylene imine and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, also doses below or above of the exemplary ranges described hereinabove are envisioned, especially considering the aforementioned factors.

As already mentioned, the compositions described herein comprising an antagonist/inhibitor of a polynucleotide or polynucleotides to be inhibited in context of the present invention being capable of decreasing or suppressing expression of FZD3 or a biologically derivative thereof, an antagonist/inhibitor of miR-31 or its 3' or 5' isoforms or variants, and/or an exosome/liposome containing said antagonist/inhibitor may be used to treat or prevent bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject.

In context of the present invention, an antagonist/inhibitor of a polynucleotide or polynucleotides to be inhibited in accordance with the present invention may be a nucleic acid molecule, a polypeptide or any other compound capable of antagonizing/inhibiting the polynucleotides to be inhibited in context of the present invention. For example, the antagonist/inhibitor to be employed in context of the present invention is an antagonist/inhibitor of miR-31 or its 5' or 3' isoforms or variants. An antagonist/inhibitor to be employed in context of the present invention may be a nucleic acid molecule capable of hybridizing to the polynucleotide to be inhibited. As described herein, nucleic acid molecules comprise all kinds of nucleotide molecules such as DNA molecules, RNA molecules, oligonucleotide thiophosphates, substituted ribo-oligonucleotides, LNA molecules (Prom, Gene (2006), 10(372), 137-141), PNA molecules, GNA (glycol nucleic acid) molecules, TNA (threose nucleic acid) molecules, morpholino polynucleotides, or antagomir (cholesterol-conjugated) polynucleotides as well as modifications thereof. The antagonist/inhibitor may hybridize to said polynucleotide to be inhibited under stringent or non-stringent conditions as described herein (for hybridization conditions for short sequences, see below), preferably under stringent conditions. Methods for determining and evaluating hybridization between nucleic acid molecules are well known in the art and are also described herein above and below. Preferably, in accordance with the present invention, by hybridizing to a polynucleotide to be inhibited in context of the present invention, the antagonist/inhibitor prevents said polynucleotide to be inhibited from decreasing or suppressing expression of FZD3 or a biologically derivative thereof, e.g., by hybridization of said polynucleotide with the mRNA (e.g., the 3'UTR thereof) of FZD3 or a biologically derivative thereof. Methods for determining and evaluating the capability of a polynucleotide to decrease or suppress the expression of FZD3 or a biologically active derivative thereof as well as methods for determining or evaluating whether the expression level of FZD3 is decreased or suppressed are described herein. Accordingly, a given compound can be assessed as an antagonist/inhibitor to be employed in context of the present invention if it is able to prevent hybridization of a polynucleotide to be inhibited in context of the present invention with the mRNA (e.g., the 3'UTR thereof) of FZD3 or a biologically derivative thereof. Accordingly, in context of the present invention, an antagonist/inhibitor may be able to at least partially reverse the effect of a polynucleotide to be inhibited in context of the present invention on the expression of FZD3 or a biologically active derivative thereof. For example, the antagonist/inhibitor to be employed in context of the present invention may be capable of reversing the effect of a polynucleotide to be inhibited on FZD3-expression by 50% or more, preferably by 60% or more, more preferably by 70% or more, more preferably by 80% or more, more preferably by 90% or more, more preferably by 95% or more, more preferably by 98% or more, and most preferably by 99% or more. That is, e.g., if a polynucleotide to be inhibited in context of the present invention is capable of decreasing or suppressing the expression of FZD3 or a biologically derivative thereof such as it amounts to an expression level of 50% compared to the normal expression level (i.e. without said polynucleotide), and the expression level increases by applying an inhibitor as described herein such that the expression level of FZD3 or a biologically derivative thereof increases to an amount of 75% compared to the normal expression level (i.e. without said polynucleotide), the effect of said polynucleotide is reversed by said inhibitor by 50%.

In one embodiment of the present invention, the antagonist/inhibitor of a polynucleotide to be inhibited in context of the present invention is a nucleic acid molecule which is capable of hybridizing to said polynucleotides to be inhibited, preferably under stringent conditions as described herein, thereby preventing said polynucleotide from hybridizing to the mRNA (e.g., the 3'UTR thereof) of FZD3 or a biologically active derivative thereof. The hybridization of said nucleic acid to be employed as an antagonist/inhibitor to a polynucleotide to be inhibited in context of the present invention may be over the entire length of said polynucleotide to be inhibited or only over a part of the sequence of said polynucleotide to be inhibited, e.g., over at least 80%, at least 85%, at least 90%, at least 95%, at least 96%, at least 97%, at least 98% or at least 99% of the sequence of said polynucleotide to be inhibited. In one embodiment of the present invention, the antagonist/inhibitor to be employed in context of the present invention may be an antisense oligonucleotide which is complementary to a polynucleotide to be inhibited in context of the present invention. Preferably, in accordance with the present invention, an antagonist/inhibitor to be employed in context of the present invention is an antisense oligonucleotide which comprises or consists of a nucleic acid molecule having a sequence complementary to any one of the sequences as shown in Table 1 hereinabove, e.g., to any one of SEQ ID NOs. 1 to 3. For example, such antisense oligonucleotides may comprise or consist of a nucleotide sequence of any one of SEQ ID NOs. 5 to 8. Generally, antagonists/inhibitors of miRNAs or siRNAs are well known in the art and customized miRNA- or siRNA-inhibitors are commercially available. For example, antagonists/inhibitors of polynucleotides to be inhibited in context of the present invention may be nucleic acid molecules such as antagomiRs (Krüzfeldt, Nature (2005), 438: 685-689) or any other 2'-O-methyl-RNA oligonucleotide having phosphorothioates bonds and a cholesterol tail, miRCURY LNA™ microRNA inhibitors (Exiqon), in vivo LNA™ miR inhibitors (Exiqon), tiny LNAs (Obad, Nat Genet (2011), 43(4): 371-378), miR-decoys or miR-sponges (Ebert, Nat Methods (2007), 4: 721-726; Bonci, Nat Med (2008), 14: 1271-1277) or the like which are capable of antagonizing/inhibiting a polynucleotide to be inhibited in context of the present invention as described hereinabove, e.g., by hybridizing to said polynucleotide. An antagonist/inhibitor might also be or derive from miRNA degrading enzymes as described in Chatterjee, Nature (2009), 461: 546-9, hammerhead ribozymes as described in Tedeschi, Drug Discov Today (2009), 14: 776-783, or antogomirzymes as described in Jadhav, Angew Chem Int Ed Engl (2009), 48(14): 2557-2560. An example of an miRCURY LNA™ microRNA inhibitor in context of the present invention is anti-miR-31 LNA as shown in SEQ ID NO: 5. In context of the present invention, the antagmoiRs, miCURY LNA™ microRNA inhibitors, in vivo LNA™ miR inhibitors, tiny LNAs, miR decoys or miR sponges may comprise a nucleic acid molecule or include a nucleic acid sequence selected from the group consisting of (a) a nucleic acid sequence being or comprising SEQ ID NO: 5;
(b) a nucleic acid sequence being or comprising SEQ ID NO: 6;
(c) a nucleic acid sequence being or comprising SEQ ID NO: 7;
(d) a nucleic acid sequence being or comprising SEQ ID NO: 8; and
(e) a nucleic acid sequence which is at least 90% or at least 95% identical to the nucleic acid sequence of any one of (a) to (d).

As mentioned, such antagonists/inhibitors may hybridize or bind to all kinds of polynucleotides to be inhibited as described herein, including microRNA, siRNA, mimic microRNA, long non-coding RNAs, snRNA, stRNA, fRNA, snRNA, snoRNA, piRNA, tasiRNA, aRNA and precursors of such polynucleotides.

The present invention relates to a composition comprising a nucleic acid molecule which hybridizes under stringent conditions with the polynucleotide consisting of the sequence shown in SEQ ID NO: 1, thereby preventing hybridization of said polynucleotide with the mRNA of FZD3, for use in treating or preventing bone disorder, like osteoporosis or cardiovascular disease, like atherosclerosis in a human subject.

The present invention relates to a composition comprising a nucleic acid molecule which hybridizes under stringent conditions to miR-31 or its 3' or 5' isoforms or variants, thereby preventing hybridization of miR-31 or its 3' or 5' isoforms or variants with the mRNA of FZD3, for use in treating or preventing osteoporosis or atherosclerosis in a human subject. Said nucleic acid molecule may be an antagomiR, a miCURY LNA™ microRNA inhibitor, an in vivo LNA™ miR inhibitor, a miR decoy or a miR sponge as described herein.

The present invention relates to a composition comprising a nucleic acid molecule which hybridizes under stringent conditions with the polynucleotide consisting of the sequence shown in SEQ ID NO: 2, thereby preventing hybridization of said polynucleotide with the mRNA of FZD3, for use in treating or preventing osteoporosis or cardiovascular diseases such as atherosclerosis in a human subject.

The present invention relates to a composition comprising a nucleic acid molecule which hybridizes under stringent conditions with the polynucleotide consisting of the sequence shown in SEQ ID NO: 3, thereby preventing hybridization of said polynucleotide with the mRNA of FZD3, for use in treating or preventing osteoporosis or cardiovascular diseases such as atherosclerosis in a human subject.

In context of the composition of the preceding paragraphs, a nucleic acid molecule which hybridizes under stringent conditions with the polynucleotide consisting of the nucleic acid sequence shown in any one of SEQ ID NOs: 1 to 3 is an antagomiR.

In context of the composition of the preceding paragraphs, a nucleic acid molecule which hybridizes under stringent conditions with the polynucleotide consisting of the nucleic acid sequence shown in any one of SEQ ID NOs: 1 to 3 is a 2'-O-methyl-RNA oligonucleotide having phosphorothioates bonds and a cholesterol tail.

In context of the composition of the preceding paragraphs, a nucleic acid molecule which hybridizes under stringent conditions with the polynucleotide consisting of the nucleic acid sequence shown in any one of SEQ ID NOs: 1 to 3 is a miRCURY LNA™ microRNA inhibitor (Exiqon).

In context of the composition of the preceding paragraphs, a nucleic acid molecule which hybridizes under stringent conditions with the polynucleotide consisting of the nucleic acid sequence shown in any one of SEQ ID NOs: 1 to 3 is an in vivo LNA™ miR inhibitors (Exiqon).

In context of the composition of the preceding paragraphs, a nucleic acid molecule which hybridizes under stringent conditions with the polynucleotide consisting of the nucleic acid sequence shown in any one of SEQ ID NOs: 1 to 3 is a miR-decoy or sponge.

Furthermore, in accordance with the present invention, the antagonist/inhibitor (i.e. in case of a nucleic acid antagonist/inhibitor) of the polynucleotide to be inhibited in context of the present invention may be cloned into a vector. The term "vector" as used herein particularly refers to plasmids, cosmids, viruses, bacteriophages and other vectors commonly used in genetic engineering. In a preferred embodiment, these vectors are suitable for the transformation of cells, like fungal cells, cells of microorganisms such as yeast or prokaryotic cells. In a particularly preferred embodiment, such vectors are suitable for stable transformation of bacterial cells, for example to transcribe the polynucleotide of the present invention.

Accordingly, in one aspect of the invention, the vector as provided is an expression vector. Generally, expression vectors have been widely described in the literature. As a rule, they may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

It is to be understood that when the vector provided herein is generated by taking advantage of an expression vector known in the prior art that already comprises a promoter suitable to be employed in context of this invention, for example expression of an inhibitor (i.e. in case of a nucleic acid inhibitor) of a polynucleotide as described hereinabove, the nucleic acid construct is inserted into that vector in a manner the resulting vector comprises only one promoter suitable to be employed in context of this invention. The skilled person knows how such insertion can be put into practice. For example, the promoter can be excised either from the nucleic acid construct or from the expression vector prior to ligation.

As a non-limiting example, the vector into which an antagonist/inhibitor (i.e. in case of a nucleic acid antagonist/inhibitor) of a polynucleotide to be inhibited in context of the present invention (i.e. which decreases or suppresses FZD3-expression) is cloned is an adenoviral, adeno-associated viral (AAV), retroviral, or nonviral minicircle-vector. Further examples of vectors suitable to comprise the inhibitor (i.e. in case of a nucleic acid inhibitor) of a polynucleotide to be inhibited in context of the present invention to form the vector described herein are known in the art. For example, a vector into which an inhibitor (i.e. in case of a nucleic acid inhibitor) of a polynucleotide to be inhibited in context of the present invention has been cloned may be miR-Vec, a retroviral expression vector (Voorhoeve, Cell (2006), 124: 1169-1181).

In an additional embodiment, the inhibitor (in case of a nucleic acid inhibitor or the coding nucleic acid sequence of a peptide inhibitor) of a polynucleotide to inhibited in context of the present invention and/or the vector into which the polynucleotide described herein is cloned may be transduced, transformed or transfected or otherwise introduced into a host cell. For example, the host cell is a eukaryotic or a prokaryotic cell, for example, a bacterial cell. As a non-limiting example, the host cell is preferably a mammalian cell. The host cell described herein is intended to be particularly useful for generating the inhibitor of a polynucleotide to be inhibited in context of the present invention.

Generally, the host cell described hereinabove may be a prokaryotic or eukaryotic cell, comprising an inhibitor of the polynucleotide to be inhibited in context of the present invention or the vector described herein or a cell derived from such a cell and containing the nucleic acid construct or the vector described herein. In a preferred embodiment, the host cell comprises, i.e. is genetically modified with nucleic acid sequence of the inhibitor of the polynucleotide to be inhibited in context of the present invention or the vector described herein in such a way that it contains the nucleic acid sequence of the inhibitor of a polynucleotide to be inhibited in context of the present invention integrated into the genome. For example, such host cell described herein may be a bacterial, yeast, or fungus cell. In one particular aspect, the host cell is capable to transcribe the nucleic acid sequence of an inhibitor of a polynucleotide which decreases or suppresses expression of FZD3 or a biologically active derivative thereof in context of the present invention. An overview of examples of different corresponding expression systems to be used for generating the host cell described herein is for instance contained in Methods in Enzymology 153 (1987), 385-516, in Bitter (Methods in Enzymology 153 (1987), 516-544), in Sawers (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), and in Griffiths, (Methods in Molecular Biology 75 (1997), 427-440). The transformation or genetically engineering of the host cell with a polynucleotide to be inhibited in context of the present invention or vector described herein can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

Furthermore, as already mentioned and in context of the present invention, it was surprisingly found that miR-31 is a valuable tool as a biomarker for aging and age-associated diseases such as osteoporosis, osteopenia, bone fracture, impaired bone homeostasis or cardiovascular diseases such as stroke, infarction, hypertension, thrombosis, vascular stenosis, coronary syndromes, vascular dementia, heart and renal failure or atherosclerosis. That is, the polynucleotides to be inhibited in context of the present invention may also serve as diagnostic or prognostic markers themselves and detection of said polynucleotides, e.g., by using compounds binding thereto, will be useful in diagnosing or predicting the progression of diseases or disorders such as osteoporosis, osteopenia, bone fracture, impaired bone homeostasis or cardiovascular diseases such as stroke, infarction, hypertension, thrombosis, vascular stenosis, coronary syndromes, vascular dementia, heart and renal failure or atherosclerosis in a subject. Accordingly, the present invention relates to a compound binding to a polynucleotide to be inhibited in context of the present invention, i.e. to a polynucleotide which is capable of decreasing or suppressing expression of FZD3 or a biologically derivative thereof as described herein, for use in diagnosing or predicting the progression of bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject.

Hence, the present invention further relates to a composition comprising
 (a) a polynucleotide capable of decreasing or suppressing expression of FZD3 or a biologically active derivative thereof as described hereinabove, and/or
 (b) a nucleic acid molecule which hybridizes to a polynucleotide capable of decreasing or suppressing expression of FZD3 or a biologically active derivative thereof as described hereinabove, and/or
 (c) an agent that binds to a polynucleotide capable of decreasing or suppressing expression of FZD3 or a biologically active derivative thereof as described hereinabove,
 for use in diagnosing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject.

The present invention also relates to a composition comprising
 (a) an agent capable of specifically interacting with (e.g., binding to) a polynucleotide being capable of decreasing or suppressing expression of FZD3 or a biologically active derivative thereof, and/or
 (b) a nucleic acid molecule which hybridizes, preferably under stringent conditions, to a polynucleotide being capable of decreasing or suppressing expression of FZD3 or a biologically active derivative thereof,
 for use in diagnosing bone disorders and/or cardiovascular disorders in a subject or for use in monitoring in vitro the treatment success of a bone disorder and/or a cardiovascular disorder as described herein.

The term "agent" as used herein, particularly in context with "agent interacting with a polynucleotide being capable of decreasing or suppressing expression of FZD3 or a biologically active derivative thereof" or "agent that binds to a polynucleotide capable of decreasing or suppressing expression of FZD3 or a biologically active derivative thereof" comprises specific proteins or protein fragments. Such proteins or protein fragments may be, e.g., antibodies or fragments thereof, small molecule inhibitors or transcription factors or modified transcription factors. Examples of such (modified) transcription factors are (modified) zinc finger proteins. Methods for generating small molecule inhibitors of polynucleotides are known in the art (Davis, Antivir Chem Chemother (2011), 21(3): 117-128). The terms "antibody" and "antibody fragment" are used herein in the broadest sense and includes, but is not limited to, monoclonal and polyclonal antibodies, multispecific antibodies (e.g., bispecific antibodies), chimeric antibodies, CDR grafted antibodies, humanized antibodies, camelized antibodies, single chain antibodies and antibody fragments and fragment constructs, e.g., F(ab')$_2$ fragments, Fab-fragments, Fv-fragments, single chain Fv-fragments (scFvs), bispecific scFvs, diabodies, single domain antibodies (dAbs) and minibodies which are capable of specifically interacting with or binding to polynucleotides to be inhibited as described herein. Methods for producing antibodies against polynucleotides are well known in the art (see, e.g., Ye, Proc Nat Acad Sci USA (2008), 105: 82-87).

Furthermore, the present invention relates to pharmaceutical compositions comprising a compound, e.g., a nucleic acid molecule or an antibody, binding to a polynucleotide to be inhibited in context of the present invention for use in diagnosing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject. In one embodiment of the present invention, the compound binding to a polynucleotide to be inhibited in context of the present invention is a nucleic acid molecule as described in context of an inhibitor capable of hybridizing to said polynucleotide as described hereinabove. Hybridization of such a binding nucleic acid molecule with said polynucleotide to be inhibited in context of the present invention can be easily detected by the skilled person using methods well known in the art and as also described herein. In one embodiment, said binding compound is a binding agent such as an antibody or a fragment thereof (such as F(ab) or F(ab)$_2$ fragments) specifically binding to said polynucleotide to be inhibited in context of the present invention, i.e. which is capable of decreasing or suppressing expression of FZD3 or a biologically derivative thereof. Binding of an antibody or a fragment thereof to a polynucleotide can be easily detected by the skilled person using methods well known in the art such as ELISA, EIA or similar methods.

Described herein is a method for diagnosing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject, said method comprising the steps of:
 (a) obtaining a biological sample from said subject which comprises a polynucleotide capable of decreasing or suppressing expression of FZD3 or a biologically active derivative thereof as described hereinabove;
 (b) contacting said sample with a nucleic acid molecule which hybridizes to the polynucleotide of (a), or with an agent that binds to a polynucleotide of (a);
 (c) detecting and evaluating hybridization or binding signal of the nucleic acid molecule of (b) or the agent of (b) with the polynucleotide of (a); and
 (d) comparing the detected and evaluated hybridization or binding signal of (c) with that correspondingly detected and evaluated hybridization or binding signal in a control sample,
wherein a stronger hybridization or a stronger binding signal in the sample of the subject compared to that of said control sample is indicative for a risk of developing or having a bone disorder and/or cardiovascular disorder.

The present invention relates to a method for diagnosing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject, said method comprising the steps of:
 (a) (i) contacting a biological sample from said subject with a nucleic acid molecule which hybridizes (preferably under stringent conditions) to a polynucleotide being capable of decreasing or suppressing expression of FZD3 and/or which hybridizes (preferably under stringent conditions) to miR-31 or its 5' or 3' isoforms or variants, or (ii) contacting said biological sample with an agent that binds to said polynucleotide being capable of decreasing or suppressing expression of FZD3 and/or that binds to miR-31 or its 5' or 3' isoforms or variants;

(b) detecting and evaluating the hybridization signal of the nucleic acid molecule of (a)(i) or detecting and evaluating the binding signal of the agent of (a)(ii) with said polynucleotide and/or said miR-31 or its 5' or 3' isoforms or variants; and (c) comparing the detected and evaluated hybridization signal of (b)(a)(i) or comparing the detected and evaluated the binding signal of (b)(a)(ii) with a correspondingly detected and evaluated hybridization or binding signal in a control sample, wherein a stronger hybridization or a stronger binding signal in the sample of the subject compared to that of said control sample is indicative for a risk of developing or having a bone disorder and/or cardiovascular disorder.

In one embodiment, the method for diagnosing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject, said method comprising the steps of (a) contacting a biological sample from said subject with a nucleic acid molecule which hybridizes (preferably under stringent conditions) to a polynucleotide being capable of decreasing or suppressing expression of FZD3 and/or which hybridizes (preferably under stringent conditions) to miR-31 or its 5' or 3' isoforms or variants;

(b) detecting and evaluating the hybridization signal of the nucleic acid molecule of (a) with said polynucleotide and/or said miR-31 or its 5' or 3' isoforms or variants; and (c) comparing the detected and evaluated hybridization signal of (b) with a correspondingly detected and evaluated hybridization signal in a control sample, wherein a stronger hybridization signal in the sample of the subject compared to that of said control sample is indicative for a risk of developing or having a bone disorder and/or cardiovascular disorder.

The nucleic acid molecules to be employed in the diagnosing methods of the present invention (i.e. hybridizing to a polynucleotide being capable of decreasing or suppressing expression of FZD3) may be of any kind of nucleic acid molecules as described herein. For example, these nucleic acid molecules may be primers (e.g., for PCR techniques) or probes (e.g., for microarray or blot assays such as dot blot, southern blot or northern blot). Primers can be used particularly in PCR techniques as described and exemplified herein. Preferably, as known in the art, one primer is complementary to a sequence of the 5'-end of the polynucleotide to be detected ("forward primer"), while the other primer is complementary to a sequence of the 3'-end of the polynucleotide to be detected ("reverse primer"). Primers for PCR techniques and the like should usually have a length of about 12 to 30 nucleotides, but they may also comprise more or less nucleotides if appropriate. The primers may not be 100% complementary to the respective sequences of the polynucleotide to be detected as long as it is still capable of hybridising to the polynucleotide, preferably under stringent conditions or such conditions as may be appropriate for the given primer as described herein below. Furthermore, primers may be conjugated to marker molecules or tagging molecules as described herein such as fluorescent dyes excited and emitting at UV/VIS or infrared wavelengths like FITC, TRITC, Texas Red, Cy-dyes, alexa dyes (Bioprobes), or the like. Probes can be generated as known in the art and usually comprise a nucleotide sequence which is complementary to a sequence of the polynucleotide to be detected. Probes are of particular useful for assays such as microarrays or blot assays (e.g., dot blot, southern blot, northern blot) as described and exemplified herein. The sequence of the probe does not have to be 100% complementary to the respective sequence of the polynucleotide to be detected as long as it is still capable of hybridising to the polynucleotide, preferably under stringent conditions. Furthermore, probes may be conjugated to marker molecules or tagging molecules as described herein such as fluorescent dyes excited and emitting at UV/VIS or infrared wavelengths like FITC, TRITC, Texas Red, Cy-dyes, alexa dyes (Bioprobes), or the like.

Hybridization conditions in context with the diagnosing methods provided herein, particularly for PCR techniques as described above, may be as follows. SSC is 3 M NaCl and 300 mM $Na_3$Citrate, adjusted to pH 7.0 with HCl. For stringent conditions, 0.1 or 0.2×SSC at 65° C. is used, preferably with addition of SDS at 1%. For intermediate conditions, 1× or 2×SSC is used, and for non-stringent conditions, 4× or 6×SSC is used, preferably with 1% SDS. The temperature is generally 65° C. or less depending on the melting temperature of the probe-target complex. As mentioned, in context with the diagnosis methods provided herein, the nucleic acid molecule may hybridize to the polynucleotide to be detected (i.e. polynucleotide being capable of decreasing or suppressing expression of FZD3) under stringent conditions.

In accordance with the present invention, determining the melting temperature ($T_m$) of a nucleic acid duplex is generally useful for many applications such as PCR, binding assays, hybridization, and the like. The $T_m$ may be defined as the temperature where 50% of a given nucleotide (such as a microRNA) is in duplex with its reverse complementary (i.e. exactly matching for formation of a double helix) sequence. $T_m$ is influenced by a number of factors well known to the person of ordinary skill, such as the length of the polynucleotide, the base composition, the sequence, the possibility to form secondary structures (such as the hairpin structures typical for micro RNA precursor molecules), and environmental conditions, such as salt (generally monovalent cation) concentration, divalent cation ($Mg^{2+}$) concentration, pH, and the presence of denaturing substances such as e.g. formamide.

In order to conduct hybridization in a PCR or any other test that requires binding of a nucleotide to its target form a double helix, the $T_m$ of the nucleotide may be determined. A number of methods for determining $T_m$ are known to the person of ordinary skill in the art. For instance, the empirical determination could be carried out by including in a buffer solution the nucleotide to be tested and its exact reverse complement, and raising the temperature from a low temperature where annealing is perfect (such as room temperature or less) to a high temperature (such as 95° C. or more) where annealing cannot take place anymore and most of the nucleotide will be single and not annealed. The change from the single to the duplex form of the nucleotide may be monitored by UV spectrometry. For example, the nucleotide and its exact fitting reverse complement may be dissolved in a buffer such as 0.1×SSC (15 mM NaCl, 1.5 mM $Na_3$Citrate, pH 7.0). UV absorbance (Abs) may be measured at 260 nm and the temperature (t) gradually changed from low to high to observe denaturation and optionally, vice versa to observe reannealing. When plotting the resulting temperature versus absorbance, an S-shaped curve may be observed, having two absorbance plateaus. The $T_m$ may then be determined as the temperature exactly halfway between the upper plateau and the lower plateau, or, alternatively, as the maximum of the first derivative dAbs/dt. (see, e.g., Thermal Analysis of DNA by UV/Visible Spectrometry, Moore, GBC application note, GBC Scientific Equipment Pty, Ltd, Braeside, Australia, http://www.gbcscientific.com/appnotes/uv_app_note_002.pdf), see also "Oligo melting temperature" by Sigma-Aldrich, St. Lois, Mo., USA (http://www.sigmaaldrich.com/life-science/custom-oligos/custom-dna/learning-center/oligos-melting-temp.html).

Of course, as is well known to the person of skill in the art, the $T_m$ can be experimentally determined by the same method for non-perfectly matching nucleotides, for RNA/DNA duplexes, for nucleotides incorporating modified or non-canonical bases (such as Inosine, generally used as a nucleotide intended to bind almost equally well any of the four canonical nucleotide bases A, C, G, T or U), or nucleotide molecules with altered backbones (e.g., locked nucleic acid—LNA, or phosphorodiamidate morpholino nucleotides; see, e.g., Summerton, Antisense Nucleic Acid Drug Dev (1997), 7(3): 187-195).

The $T_m$ determined experimentally is only valid for the conditions at which it was measured. For other conditions (e.g., salt (monovalent cation) concentration, divalent cation concentration), formulas may be used that allow an estimation of the $T_m$ under different conditions (see below).

Alternatively, the approximate $T_m$ of a given nucleotide sequence can be calculated. A number of methods are known to the person of ordinary skill in the arts, such as the GC content method, the nearest neighbour method and others. Generally, the nearest neighbour method results in more accurate estimations, although none of these methods is able to predict the $T_m$ of a given nucleotide sequence with absolute accuracy, so that a few ° C. deviation (generally assumed to be 5-10° C.) must be taken into account. Accordingly, in most hybridization, annealing, primer extension or other methods that rely on the formation of a nucleotide duplex, the temperature at which the experiment is performed is chosen about 5-10° C. below the theoretically calculated $T_m$, in order to ensure perfect duplex formation. Of course, as is well known in the art of molecular biology, hybridization conditions may be optimized, e.g., by testing the hybridization/primer annealing/PCR or other experiment that relies on nucleotide duplex formation at various temperature and other conditions and determining the conditions at which the best result is obtained.

A simple way to calculate estimated $T_m$ values is based on the GC content of the nucleotide sequence (see, e.g., for short nucleotide sequences, the "Wallace rule", Wallace, Nucleic Acids Res (1979), 6: 3543; for longer nucleotides, see below). Briefly, different equations are used for calculating the estimated $T_m$ of duplexes containing DNA and RNA, as RNA bases tend to pair more strongly, resulting in higher $T_m$ values for the same sequence compared to DNA-DNA duplexes (generally, RNA-RNA duplexes are most stable, RNA-DNA hybrids are of intermediate stability, and DNA-DNA duplexes are least stable for the same nucleotide sequence). One simple equation is the "Wallace rule", where the melting temperature is determined as two ° C. for each A/T pair and 4° C. for each G/C pair in the sequence (Td=2(#A/T)+4(#C/G). This equation would results in an estimate for the melting temperature at a situation where one nucleotide is membrane-bound at a salt concentration of 0.9 M. Where both nucleotides forming the duplex are in solution the $T_m$ would be slightly lower than calculated by this formula (about 7-8° C. lower). For nucleotides longer than about 14 to 20 bases, the methods described in Howley, J Biol Chem (1979), 254: 4876 may be used. Briefly, for DNA-DNA duplexes, $T_m$ is calculated as $T_m=81.5+16.6 \log [Na^+]+41(GC \%)-500/L-0.62 F$ where $Na^+$ is the molar concentration of monovalent cations, GC % is the fraction of GC nucleotides versus the total number of nucleotides (being a value between 0 and 1), L is the nucleotide length, and F is the percentage of formamide if present in the solution (being a value between 0 and 100). When calculating estimated values for RNA-DNA hybrids or RNA-RNA duplexes, a slightly different formula is used ($T_m=79.8+18.5 \log [Na^+]+58.4 (\% GC)+11.8 (\% GC)^2-820/L-0.35F$), while for DNA-RNA hybrids (the RNA being the molecule in solution), the formula is $T_m=79.8+18.5 \log [Na^+]+58.4 (\% GC)+11.8 (\% GC)^2-820/L-0.50F$.

An improved method for estimation of a $T_m$ value is the nearest neighbour method, so called because it takes into account not only the percentage of G/C interactions in the duplex, but also the nearest neighbour of each nucleotide, effectively adding up the binding energies of each dinucleotide in the sequence. This method results in different estimation of $T_m$ for different nucleotide sequences having the same G content, yielding a more precise estimation for $T_m$ than the above-mentioned GC content method (see for overview, e.g., SantaLucia, Proc Natl Acad Sci USA (1998), 95: 1460-1465; for DNA see, e.g., Breslauer, Proc Natl Acad Sci USA (1986), 83, 3746-3750; for RNA see, e.g., Freier, Proc Natl Acad Sci (1986), 83, 9373-9377). By way of example, the formula $T_m=(1000\Delta H/A+\Delta S+R^* \ln(C/4))-273.15+16.6 \log [Na^+]$ may be used, where $\Delta H$ (Kcal/mol) is the sum of the nearest-neighbour enthalpy changes for hybrids, A is a small constant containing corrections for helix initiation, $\Delta S$ is the sum of the nearest-neighbour entropy changes, R is the Gas Constant (1.99 cal/(K*mol)), C is the concentration of the nucleotide, and $Na^+$ is the concentration of monovalent cations in the solution. The $\Delta H$ and $\Delta S$ values to be used this calculation for DNA and RNA duplexes are shown in the table (formula example and values from Sigma-.Aldrich, reference see above).

Thermodynamic parameters for nearest-neighbour melting temperature formula.

| Interaction | DNA | | RNA | |
| --- | --- | --- | --- | --- |
| | $\Delta H$ | $\Delta S$ | $\Delta H$ | $\Delta S$ |
| AA/TT | −9.1 | −24.0 | −6.6 | −18.4 |
| AT/TA | −8.6 | −23.9 | −5.7 | −15.5 |
| TA/AT | −6.0 | −16.9 | −8.1 | −22.6 |
| CA/GT | −5.8 | −12.9 | −10.5 | −27.8 |
| GT/CA | −6.5 | −17.3 | −10.2 | −26.2 |
| CT/GA | −7.8 | −20.8 | −7.6 | −19.2 |
| GA/CT | −5.6 | −13.5 | −13.3 | −35.5 |
| CG/GC | −11.9 | −27.8 | −8.0 | −19.4 |
| GC/CG | −11.1 | −26.7 | −14.2 | −34.9 |
| GG/CC | −11.0 | −26.6 | −12.2 | −29.7 |
| Initiation | 0.0 | −10.8 | 0.0 | −10.8 |

In general, these methods will result in estimates, not absolutely accurate values. Moreover, conditions like immobilization (see above), impurities, and nucleotide modification may all influence the actual $T_m$ value of a given duplex or hybrid.

In some cases, an empirical approach must be used, while in others the empirical determination may be used to improve on the estimate derived from the calculation. Generally, modifications like biotin, fluorescent dyes and the like will likely result in a lower $T_m$, while some modifications (like the backbone modification used in LNAs) may results in a higher $T_m$. For LNA backbones, the nucleotides containing such backbones can, as an approximation, be assumed to be RNA nucleotides (resulting in more stable binding and hence higher $T_m$ values). Therefore, an LNA-RNA hybrid could be calculated Like the corresponding RNA-RNA hybrid, while a nucleotide containing some LNA nucleotides and some DNA nucleotides could be calculated on the basis of mixed energy values (for LNA nucleotides RNA values could be used, for DNA nucleotides DNA values are used).

For ease of use in molecular biology, the above methods are also implemented on a number of servers for public use, such as http://biophysics.idtdna.com/ or http://www.biophp.org/minitools/melting_temperature/demo.php.

Thus, the person of ordinary skill is easily able to determine an estimate for the melting temperature for a given nucleotide sequence. For instance, for SEQ ID NO: 1, a $T_m$ of between 50 and 54.4° C. could be obtained, while for SEQ ID NO: 3 (the miRNA 31 precursor sequence), between 67.4 and 76.2° C. could be obtained. These values are calculated for 15 mM monovalent cation (salt) concentration, which corresponds approximately to 0.1×SSC buffer, that is, to stringent hybridization conditions (see further above), with the proviso that the temperature must be adjusted accordingly (For the precursor, in this case the 65° C. temperature condition could be tested, while for the shorter mature miRNA, the temperature must be lowered to about 45° C., depending on further factors like pH, divalent cations, target concentration and the like. Correspondingly, an estimate for variations of a given sequence may be obtained (providing that the target is matched in sequence).

The detection of a miRNA can be achieved by various methods. For instance, miRNA may be detected and quantified by deep sequencing methods, relying upon the fact that more sequence reads are obtained from miRNA molecules present more abundantly. Such methods are well known to the person of skill and described, inter alia, by Friedländer., Nat Biotechnol (2008), 26(4): 407-415; Koh, BMC Genomics (2010), 10(11) Suppl 1: S6; Creighton, Brief Bioinform (2009), 10 (5): 490-497. miRNA abundance may further be determined by array technology. For instance, the Ncode human miRNA array available from Invitrogen, Carlsbad, Calif., USA may be used to determine relative abundance of a large number of human miRNAs in a sample. Chip arrays for detection and determination of relative abundance of miR-NAs are also available from Affymetrix, Santa Clara, Calif., USA, e.g., the U133 Plus 2.0. Affymetrix expression array (see. e.g., Ivanov, J Biol Chem (2010), 285: 22809-22817). Arrays based upon LNA backbone probes (miRCURY LNA™ arrays) are, e.g., available from Exiqon, Vedbaek Denmark.

Further, the presence and relative abundance of a miRNA in a sample can be assayed by in situ detection. Although the detection of microRNAs (miRNAs) in situ presents several technical challenges due to their short length, this can be overcome, e.g., by using digoxygenin-labeled locked nucleic acid (LNA) oligonucleotide probes for detection (see, e.g., Sweetman, Methods Mol Biol (2011), 732: 1-8). Using this method, the subcellular distribution of miRNAs can be detected. In situ methods are also useful for resolution of miRNA distribution on a tissue and organism level (see, e.g., Diez-Roux, PLoS Biol (2011), 18; 9(1): e1000582). Further works by others have demonstrated the feasibility of in situ hybridization and fluorescence-based detection for miRNA detection and relative abundance determination (Lu J, Methods Mol Biol (2011), 680: 77-88; Mansfield, Methods. (2010), 52(4): 271-280; Gupta, Methods Mol Biol (2011), 676: 73-83; Debernardi, Methods Mol Biol (2010), 667: 33-45; Silahtaroglu, Methods Mol Biol (2010), 659: 165-171, also working with LNA nucleotides as probes; and Nuovo, Methods (2010), 52(4): 307-315, demonstrating the method also for paraffin-embedded samples).

As mentioned, another example of a method of miRNA detection and quantification which may be employed in context of the diagnosis methods provided herein is quantitative PCR (qPCR). As the miRNA is a relatively short molecule, it is possible to extend its length by adding Adenosine monomers to the strand (a technique known as polyadenylation) first before reverse transcription and amplification. Briefly, the RNA may be extracted from a sample by a suitable reagent (e.g. Trizol reagent available from the above mentioned Invitrogen), poyadenylated in the presence of ATP and poly(A) polymerase, reverse transcribed into DNA using a poly(T) adapter and 5' RACE sequence, and amplified using a forward primer derived from the 3' end of the miRNA and a reverse RACE primer (for details concerning primer design, RACE sequence etc. see. e.g., Shi, BioTechniques (2005), 39: 519-525. Improvements of this technique include designing the RACE primer with a nucleotide at its 3' end (constituting an A, C, or G, but not a T, so to exclude priming anywhere on the poly A sequence and enforce priming on the miRNA sequence; see also Reichenstein., J Virol Methods (2010), 163(2): 323-328).

As an example, the following primers may be used for detection and quantification of miR-31 (SEQ ID NO: 1): Forward primer. 5'-ACGCGGCAAGATGCTGGCA-3' (SEQ ID NO: 29), Reverse primer. 5'-CAGTGCTGGGTC-CGAGTGA-3' (SEQ ID NO: 30) (see Wang., Dis Markers (2009), 26(1): 27-34). Further examples for PCR quantification of miRNA 31 include Liu, J Clin Invest (2010), 120(4): 1298-1309 (also detailing microarray assaying of miRNA31). Further, miRNA detection and quantitation using the Taqman system is readily available from Applied Biosystems/Life technologies, Carlsbad, Calif., USA (see, e.g., http://www3.appliedbiosystems.com/cms/groups/mcb_marketing/documents/generaldocuments/cms_042142.pdf) as also described and exemplified herein in the appended Examples. Another example for quantitative PCR determination of mir31 uses a stem-loop primer for reverse transcription and a forward and reverse primers for PCR amplification of the miR-31 cDNA. Examples of such primers include for the stem-loop primer: gtcgtatccagtgcagggtccgaggtat-tcgcactggatacgacagctatgcctg (SEQ ID NO: 31); for the forward primer: tgaccgaggcaagatgc (SEQ ID NO: 32); and for the reverse primer: gtgcagggtccgaggt (SEQ ID NO: 33). Forward and reverse primer overlap by one nucleotide on the miR-31 sequence, this however is not enough to cause a primer dimer (for PCR conditions and further details see Ivanov, J Biol Chem (2010), 285: 22809-22817).

In another embodiment, the method for diagnosing bone disorders and/or cardiovascular disorders such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis in a subject, said method comprising the steps of
  (a) contacting a biological sample from said subject with an agent that binds to said polynucleotide being capable of decreasing or suppressing expression of FZD3 and/or that binds to miR-31 or its 5' or 3' isoforms or variants;

(b) detecting and evaluating the binding signal of the agent of (a) with said polynucleotide and/or said miR-31 or its 5' or 3' isoforms or variants; and (c) comparing the detected and evaluated the binding signal of (b) with a correspondingly detected and evaluated binding signal in a control sample, wherein a stronger binding signal in the sample of the subject compared to that of said control sample is indicative for a risk of developing or having a bone disorder and/or cardiovascular disorder.

In one embodiment of the diagnostic method provided herein, a method is provided that is a method for diagnosing bone disorders and/or cardiovascular disorders in a subject, said method comprising the steps of:

(a) detecting via a PCR method the expression level and/or quantity of miR-31 (and isoforms and variants thereof as defined herein) in a biological text sample; and (b) comparing the detected expression level and/or quantity of said miR-31 (and isoforms and variants as defined herein) in said biological sample with a corresponding expression level and/or quantity of said miR-31 in a control sample.

Again, a control sample may be a sample derived from a disease-negative (or healthy) control patient. This would be a "negative control". However, it is also envisaged, for example as a second or additional control, that such a control sample is a sample derived from a patient who suffers from said bone disease and/or said cardiovascular disorder. This would be a positive control. The sample may be blood, blood serum, blood plasma or another biological fluid. As shown in the appended examples, plasma and serum are very useful. Methods for the assessment of nucleic acid molecules, also of mino RNAs are well known in the art. Such methods comprise e.g. PCR, also and in particular quantitative PCR as well as real-time qPCR; see, e.g. Chen (2011) Methods Mol. Biol. 687, 113-134, or Mestdagh (2008) Nuc. Acid Res. 36(21): e143.

In one embodiment (and as illustrated in the examples) the disorder to be assessed or diagnosed in accordance with the invention is a bone disorder, i.e. an osteopenia or osteoporosis and the like.

The invention also provides a method for the detection of a polynucleotide being capable of decreasing or suppressing expression of FZD3 and/or which hybridizes to miR-31 or its 5' or 3' isoforms or variants. A convenient method is based upon polymerase chain reaction (PCR), as this method is rapid, specific and sensitive. For PCR, a primer is required that hybridizes specifically to the target nucleic acid. Moreover, a second primer is required to generate a PCR product by repeated cycles of primer annealing, primer extension, and denaturing. The primer is chosen to maximize hybridization to the target nucleic acid while minimizing cross-hybridization to other nucleic acids present in the sample. Examples of primer sequences and of calculating the optimal hybridization temperature and other conditions for any chosen primer sequence are given hereinbelow.

Accordingly, the invention provides a method for diagnosing bone disorders and/or cardiovascular disorders in a subject, said method comprising the steps of:

(a) contacting a biological sample from said subject with a first primer molecule which hybridizes to a polynucleotide being capable of decreasing or suppressing expression of FZD3 and/or which hybridizes to miR-31 or its 5' or 3' isoforms or variants, forming a hybridization complex;

(b) contacting the hybridization complex of step (a) with a second primer and a polymerase capable of extending the primer;

(c) repeatedly causing the primers to be extended by polymerase, the product to denature, and the primers to hybridize to the denatured product of polymerase extension, (d) detecting and evaluating the product of step (c), resulting in a value reflecting the amount of the polynucleotide being capable of decreasing or suppressing expression of FZD3 and/or which hybridizes to miR-31 or its 5' or 3' isoforms or variants to which the first primer nucleic acid has hybridized;

(e) comparing the detected and evaluated value of (d) with a correspondingly detected and evaluated value in a control sample, wherein a higher value resulting from the sample of the subject compared to that of said control sample is indicative for a risk of developing or having a bone disorder and/or cardiovascular disorder.

Where the polynucleotide being capable of decreasing or suppressing expression of FZD3 and/or which hybridizes to miR-31 or its 5' or 3' isoforms or variants (the target nucleotide) is an RNA molecule, the method preferably comprises the step of reverse transcription of the target nucleotide. Reverse transcription may be carried out by a primer that overlaps a sufficient portion of the target molecule, preferably at its 3' end. The length of the target molecule may be extended by the step of polyadenylation prior to reverse transcription. In this case, the reverse transcription primer comprises a poly(t) sequence and at least one nucleotide complementary to the target sequence. Preferably, said nucleotide is not a T. More preferably, the primer comprises the complement of two nucleotides of the target sequence, wherein the first (the penultimate nucleotide at the 3' end of the primer) is not a T.

In another preferred embodiment, the reverse primer is a stem-loop primer which comprises a short overlap with the (complement of the) target sequence and a stem-loop structure, as described and exemplified below.

In principle, the diagnosis methods described herein may employ a PCR technique (e.g., qPCR, RT-PCR, qRT-PCR, RT-qPCR or Light Cycler®) or other methods suitable to detect presence and/or amounts of polynucleotides. In the diagnosis methods of the present invention, the presence and/or amount of a polynucleotide which is capable of decreasing or suppressing expression of FZD3 or a biologically derivative thereof and/or of miR-31 or its 3' or 5' isoforms or variants is evaluated in a sample of a subject. PCR techniques and other methods suitable for this purpose are known in the art and are also described and exemplified herein. If the amount of said polynucleotide and/or of miR-31 or its 3' or 5' isoforms or variants is elevated compared to a control sample, the risk of developing or having a bone disorder and/or cardiovascular disorder is increased. For example, for the case of employment of a qPCR technique, total RNA of a subject's biological sample may be transcribed into cDNA. Then, specific primers hybridizing to said polynucleotide and/or of miR-31 or its 3' or 5' isoforms or variants may be used for detection. The amount of polynucleotide and/or of miR-31 or its 3' or 5' isoforms or variants detected in the subject's sample may then be compared to the amount of polynucleotide and/or of miR-31 or its 3' or 5' isoforms or variants of a control sample. The higher the amount is in the subject's sample compared to the control sample, the higher is the risk of developing or having a bone disorder and/or cardiovascular disorder.

In context with the diagnosing methods described herein, a hybridization or binding signal of the subject sample of (a) which is at least 50%, 60%, 70% or 75% higher than that of the control sample may be indicative for a risk of developing or having a bone disorder and/or cardiovascular disorder such as osteoporosis, osteopenia, bone fracture, impaired bone homeostasis, or cardiovascular diseases such as stroke, infarction, hypertension, thrombosis, vascular stenosis, coronary syndromes, vascular dementia, heart and renal failure or atherosclerosis. The polynucleotide capable of decreasing or suppressing expression of FZD3 or a biologically active derivative thereof is preferably a polynucleotide to be inhibited in context of the present invention. Examples for biological samples in context of the present invention are blood, serum, plasma, other blood derived products, saliva, sperm fluid, vaginal fluid, urine, cerebrospinal fluid, or the like. In one embodiment, the method is an in vitro method. In context of the present invention, the nucleic acid molecule hybridizing to the polynucleotide to be inhibited in context of the present invention or the agent, e.g., an antibody, binding to the polynucleotide as described hereinabove may further be conjugated to a marker or tagging molecule. Examples for such marker molecules for nucleic acids are fluorescent dyes excited and emitting at UV/VIS or infrared wavelengths like FITC, TRITC, Texas Red, Cy-dyes, alexa dyes (Bioprobes), etc. Examples for such marker/tagging molecules for antibodies are enzymes like horse radish peroxidase, alkaline phosphatase or fluorescent dyes excited and emitting at UV/VIS or infrared wavelengths like FITC, TRITC, Texas Red, Cy-dyes, alexa dyes, etc.

The appended sequence listing is part of the description.

(A) Pre-senescent (PD13) and senescent (PD53) endothelial cells were stained for senescence associated β-galactosidase activity. (B) Apoptotic cell death of HUVECs 48 h after secretion into ASC or HUVEC medium was measured using Annexin V-FITC and PI staining (N=3). (C) Representative microscope pictures of two different ASC lines. (D) ASCs were stained for expression of cell surface markers using flow cytometry. Abbreviations: ASC, adipose-derived stem cell.

Figure 2:
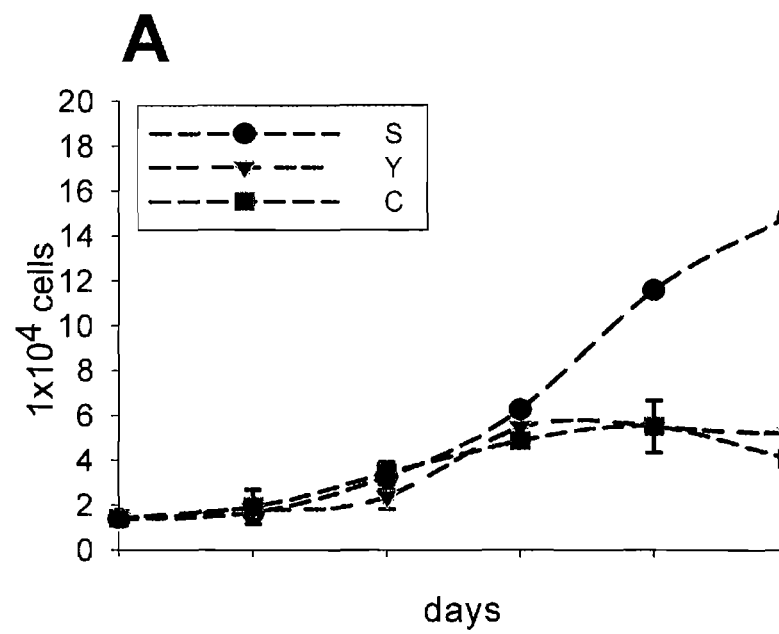
Figure 2:
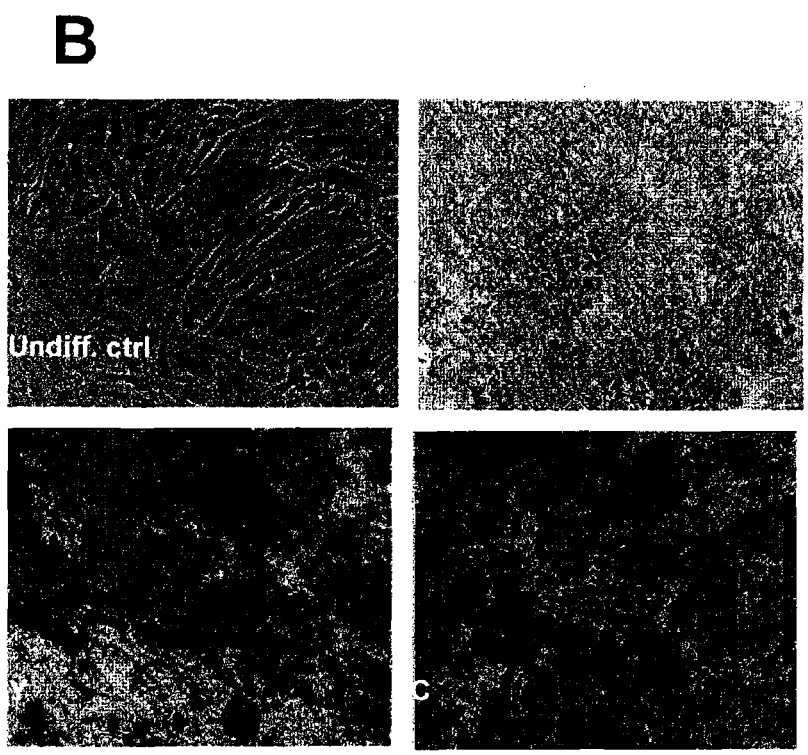

FIG. 2: Effects of HUVEC supernatants on proliferation and differentiation capacity of ASCs.

(A) ASCs were cultivated in the presence of conditioned medium from pre-senescent (PD13) and senescent (PD53) cells and in control medium. Viable cell numbers were analysed using a hematocytometer and trypan blue staining. Error bars indicate the standard deviations of 3 independent measurements. (B) Treated cells were differentiated into the osteogenic lineage detected using Alizarin Red staining. Representative pictures of 3 independent experiments are shown. Abbreviations: Undiff ctrl, undifferentiated control; S, senescent; Y, young; C, control.

Figure 3:
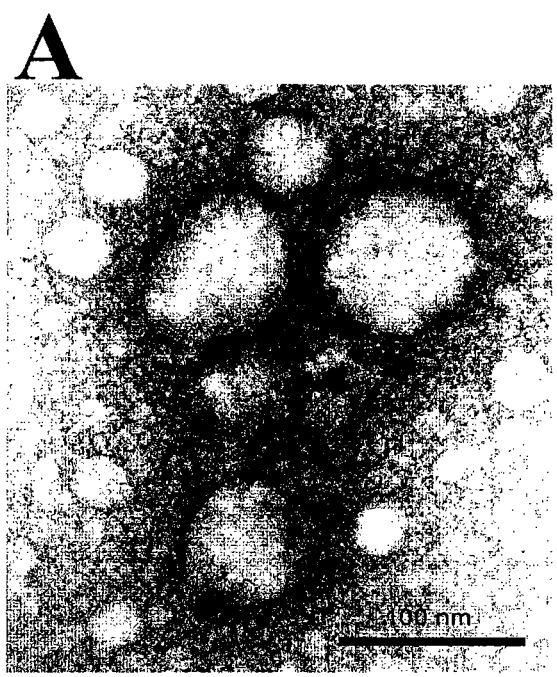
Figure 3:
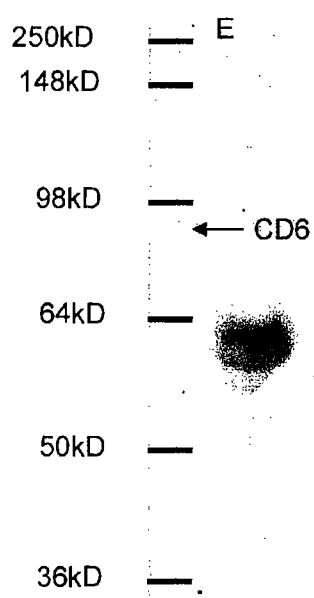
Figure 3:
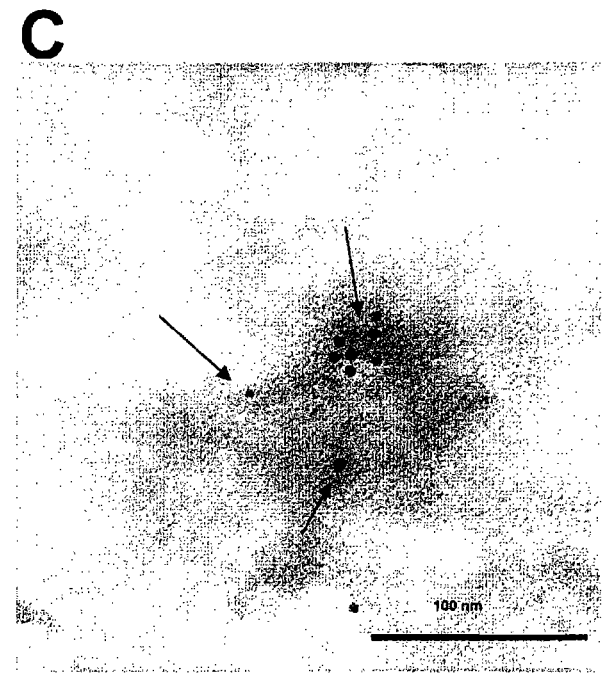
Figure 3:
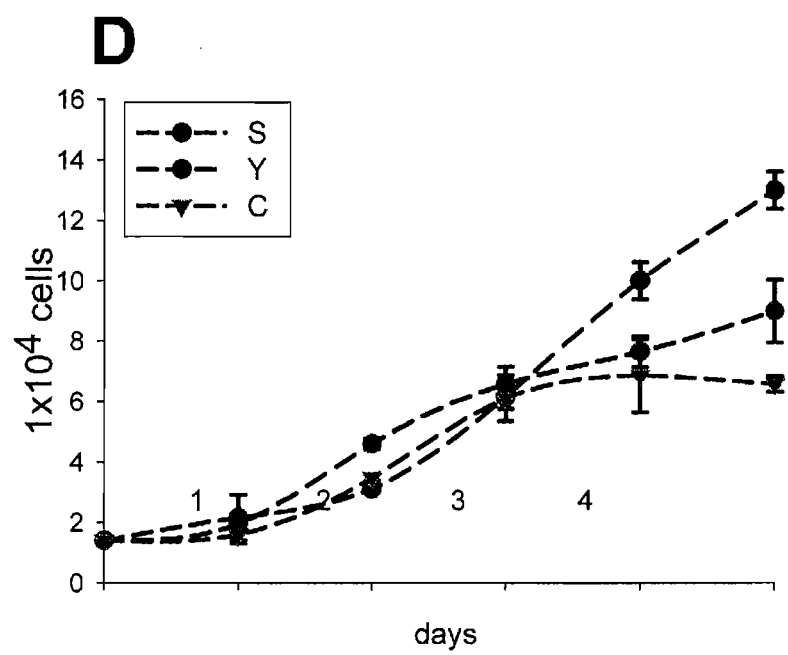
Figure 3:
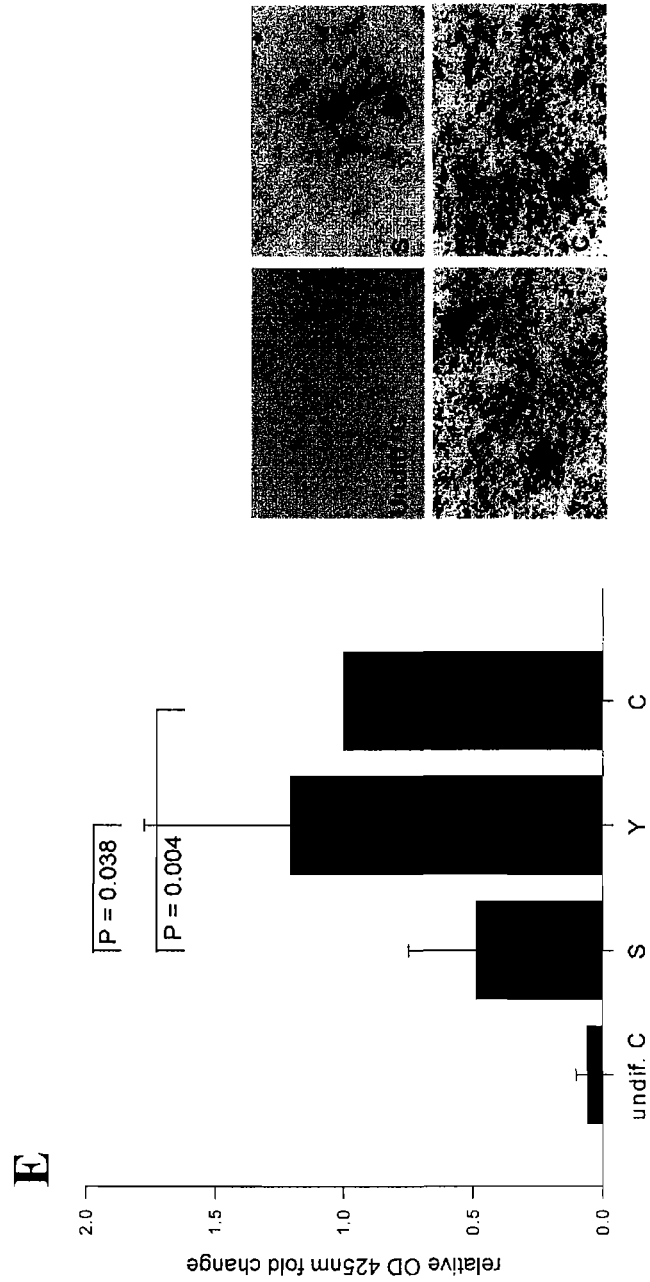

FIG. 3: Exosomes of senescent HUVECs increase proliferation and reduce differentiation capacity of ASCs.

(A) Electron microscopy of HUVEC derived exosomes. The image shows typical cup-shaped vesicles of ~50 to 100 nm in diameter. (B) Western blot analysis shows exosome marker protein CD63. (C) Exosomes were labelled with anti-CD63 antibody and visualized by electron microscopy. (D) ASCs were cultivated in the presence of exosomes derived from pre-senescent (PD13) and senescent (PD53) cells and in control medium. Cell numbers were detected using a hematocytometer and trypan blue staining. Error bars indicate the standard deviations of 3 independent measurements. (E) Treated cells were differentiated into the osteogenic lineage. Ca deposits as marker for osteogenesis was detected by Alizarin Red staining. Representative pictures of 3 independent experiments are shown. Abbreviations: Undiff ctrl, undifferentiated control; S, senescent; Y, young; C, control.

Figure 4:
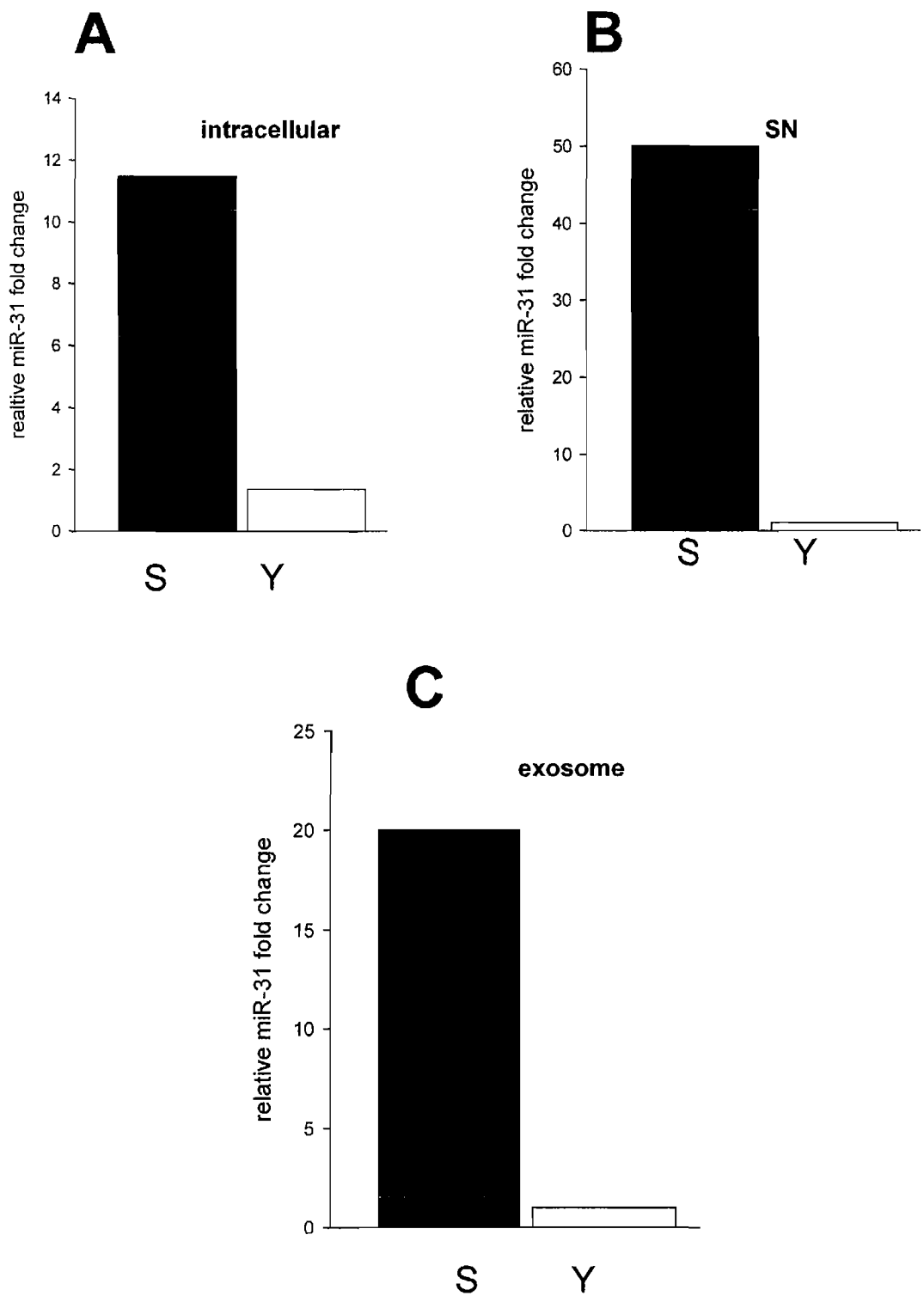
Figure 4:
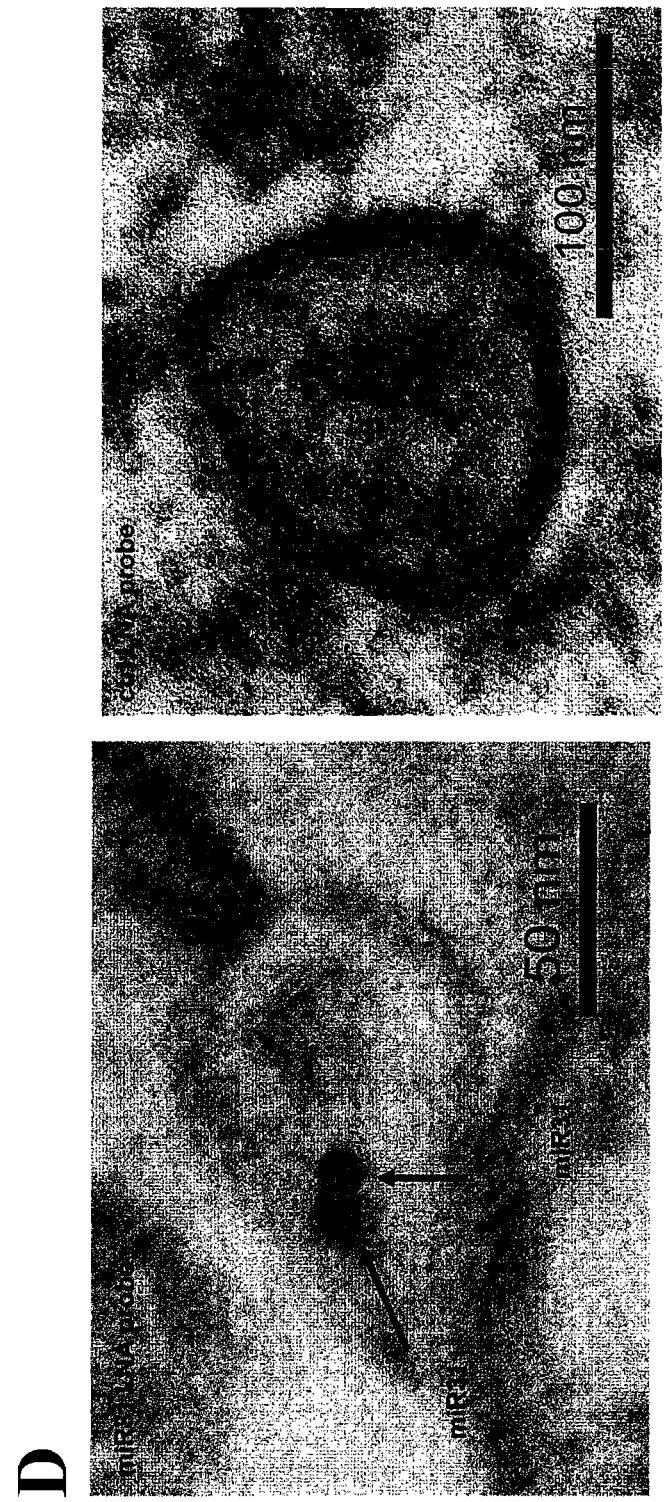

FIG. 4: MiR-31 is increasedly secreted by senescent endothelial cells.

MiR-31 is upregulated in senescent HUVECs (A) as well as in SN (B) and exosomes (C) derived from senescent HUVECs. (D) Localization of miR-31 within exosomes by electron microscopy in situ hybridization (EM-ISH). Abbreviations: S, senescent; Y, young; SN, supernatant.

Figure 5:
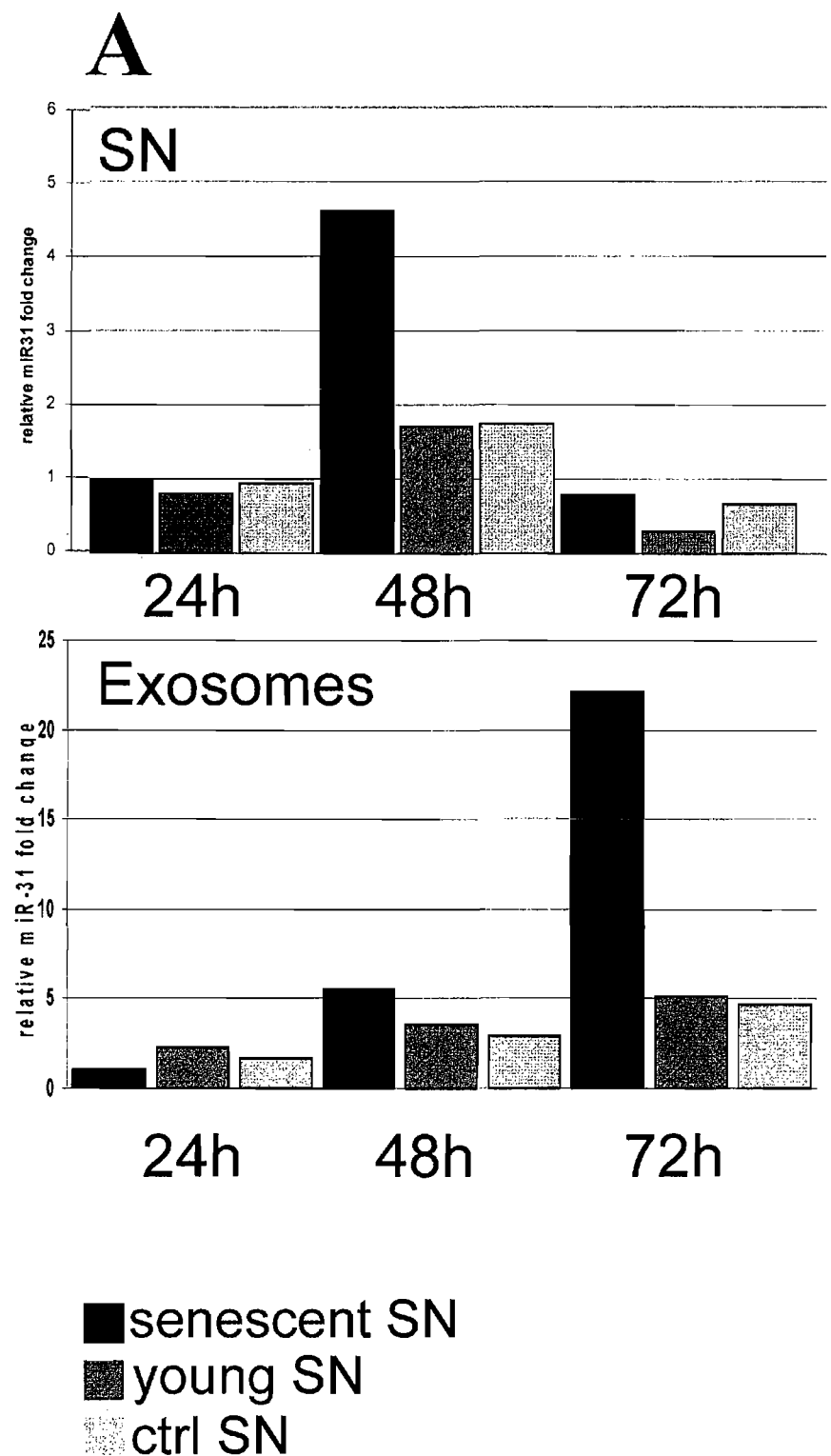
Figure 5:
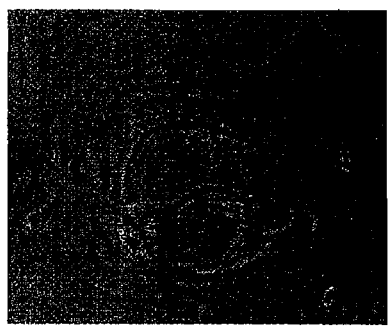
Figure 5:
Figure 5:
Figure 5:
Figure 5:
Figure 5:
Figure 5:
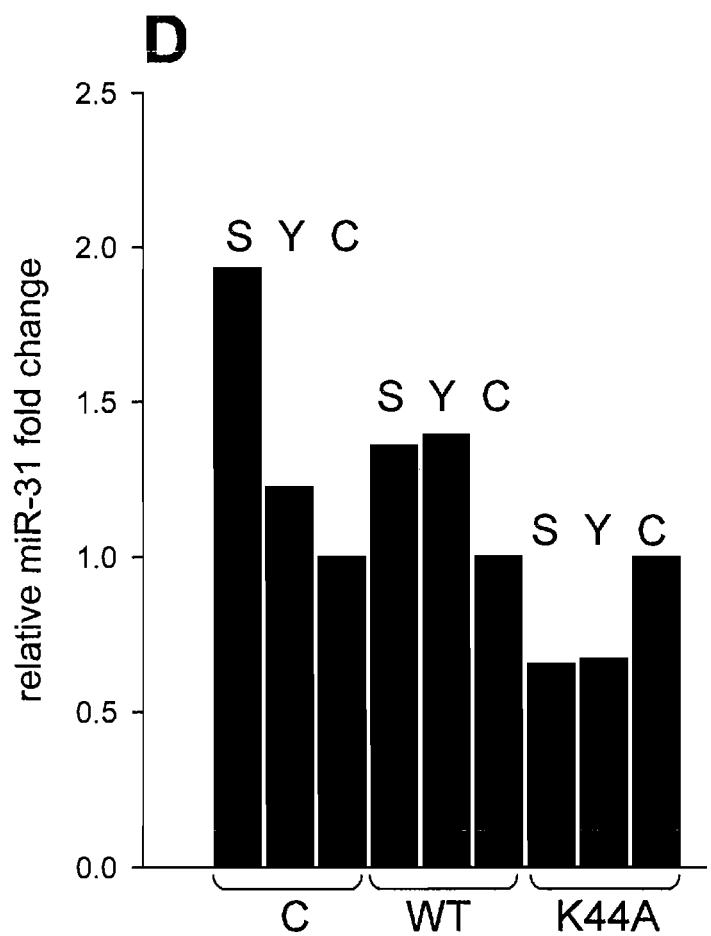

FIG. 5: ASCs take up exosomes derived from HUVECs.

(A) Intracellular levels of miR-31 in ASC after treatment with SN or exosomes derived from pre-senescent and senescent HUVECs. (B) Representative image of stable transfected senescent endothelial cell expressing GFP. (C) Representative image of ASCs after uptake of GFP-positive exosome 48 h after incubation. (D) ASCs showing decreased levels of intracellular miR-31 levels after transfection with the negative dominant dynamin construct (K44A) and treatment with exosomes. Abbreviations: SN, supernatant; S, senescent; Y, young; C, control; WT, wild type.

Figure 6:
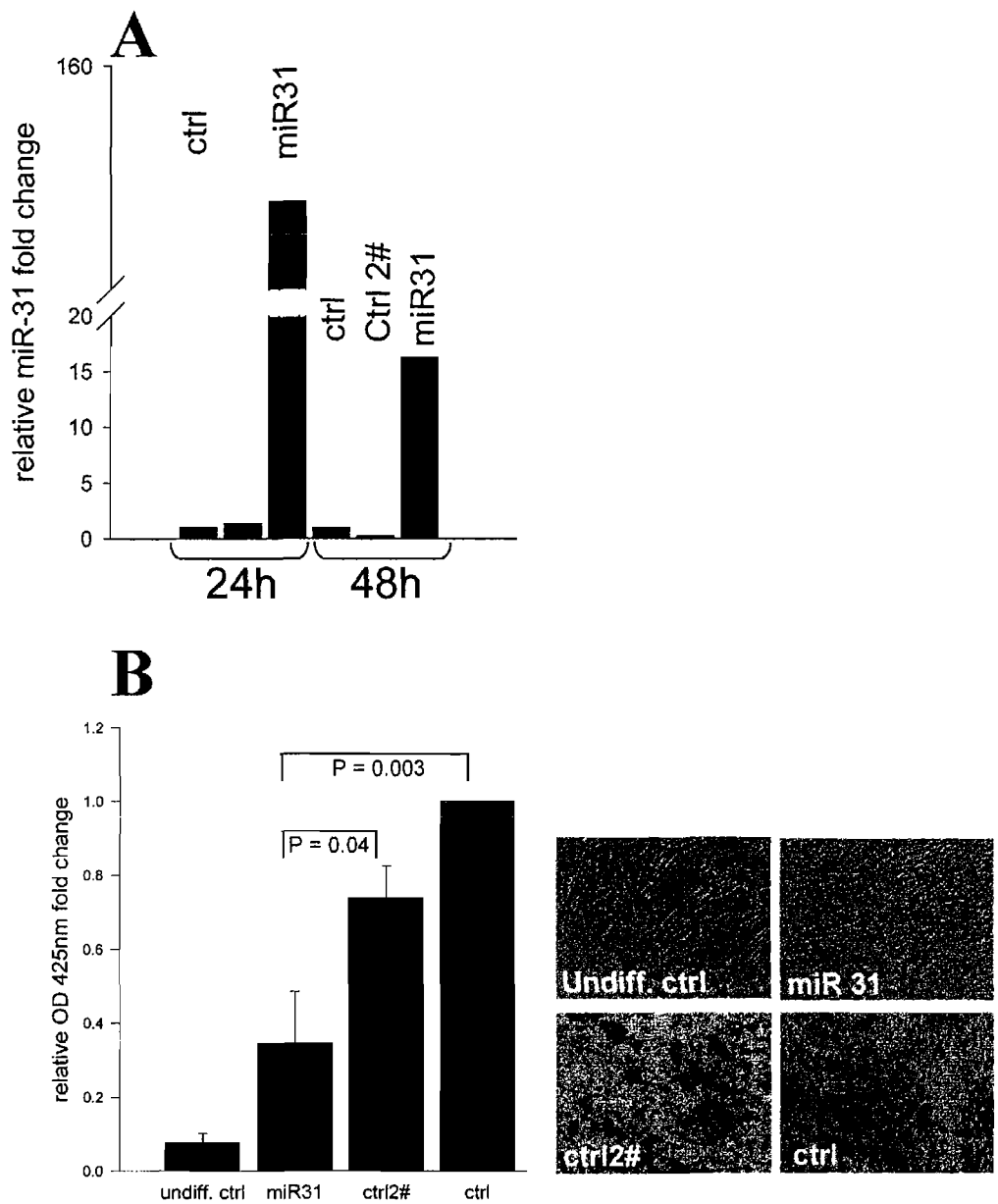

FIG. 6: miR-31 alone reduces osteogenic differentiation of ASCs.

(A) Elevated miR-31 levels after transient transfection were confirmed using TaqMan assay. (B) MiR-31 transfected cells were differentiated into the osteogenic lineage (N=3). Differentiation was detected using Alizarin Red staining. Representative images of 3 independent experiments are shown. Abbreviations: Undiff ctrl, undifferentiated control; ctrl, control.

Figure 7:
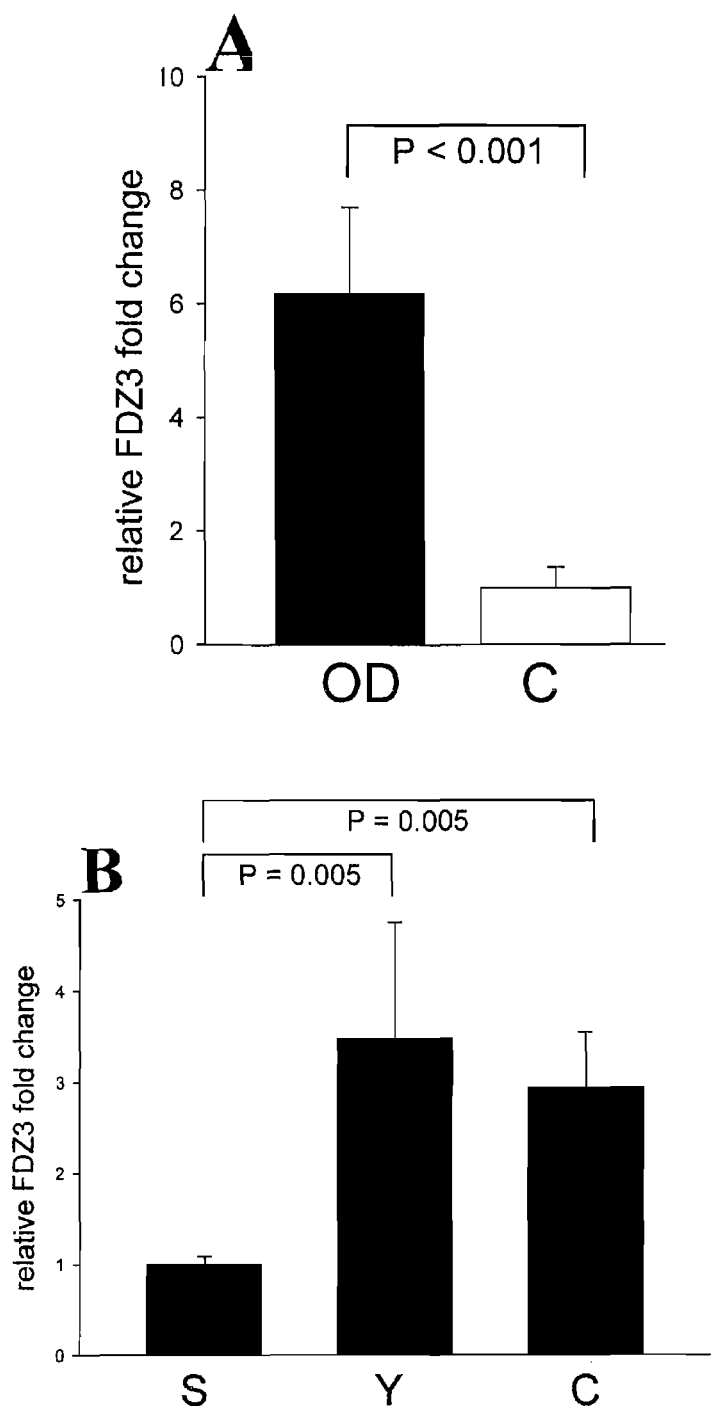
Figure 7:
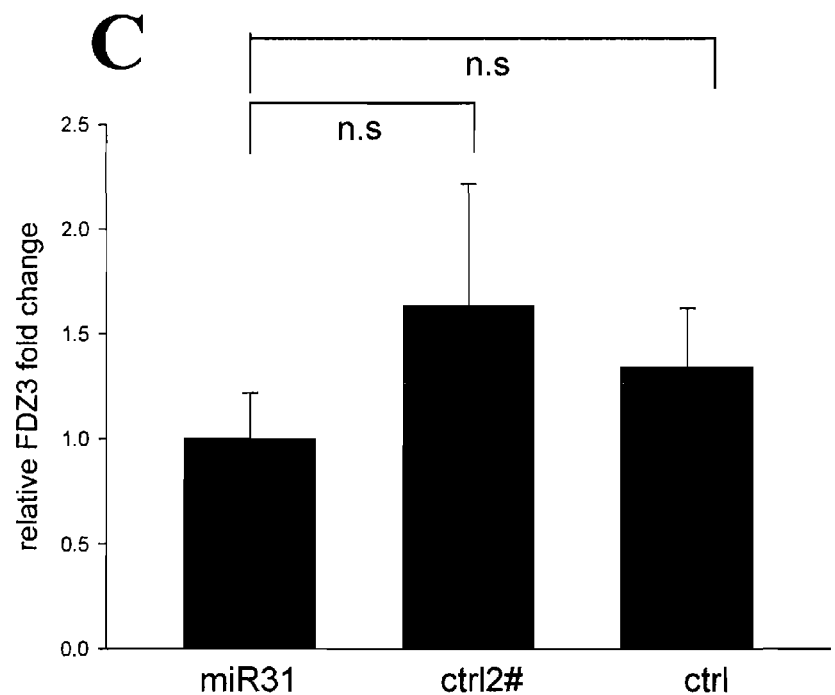

FIG. 7: FDZ3 is a target of miR-31 in ASCs.

(A) Significant upregulation of FDZ3 mRNA 4 days after osteogenic differentiation start. (B) Significant downregulation of FDZ3 mRNA in ASCs treated with senescent versus young exosomes. (C) Downregulation of FDZ3 mRNA after transient transfection of ASCs with 10 nM miR-31 precursor. Abbreviations: OD, osteogenic differentiation; S, senescent; Y, young; C, control; ctrl, control.

Figure 8:
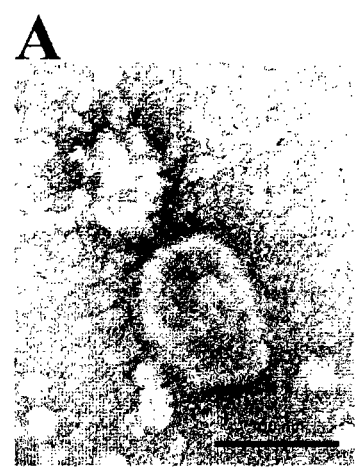
Figure 8:
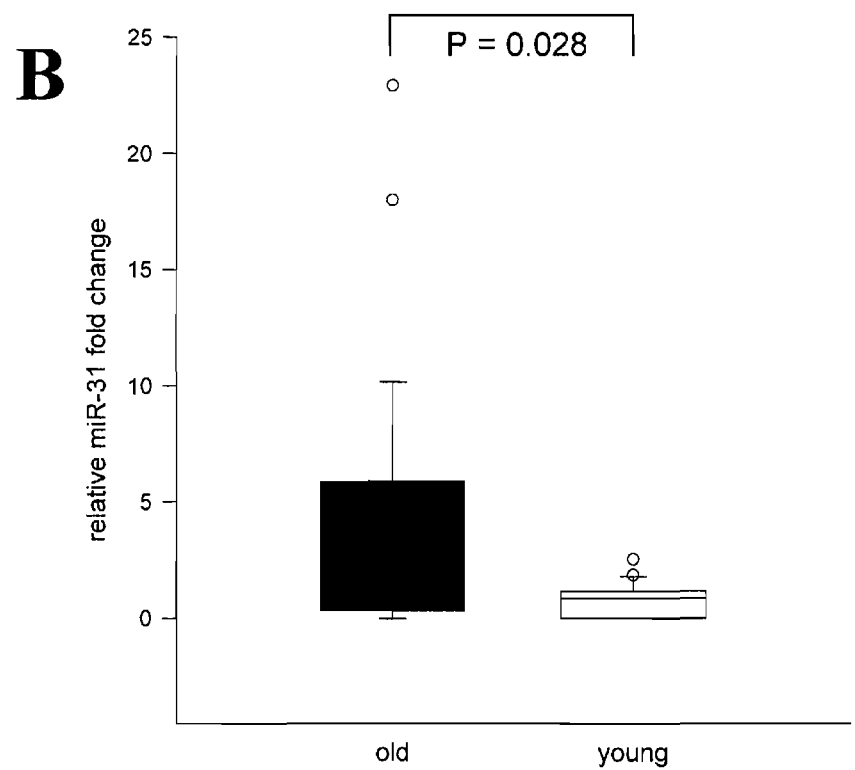
Figure 8:
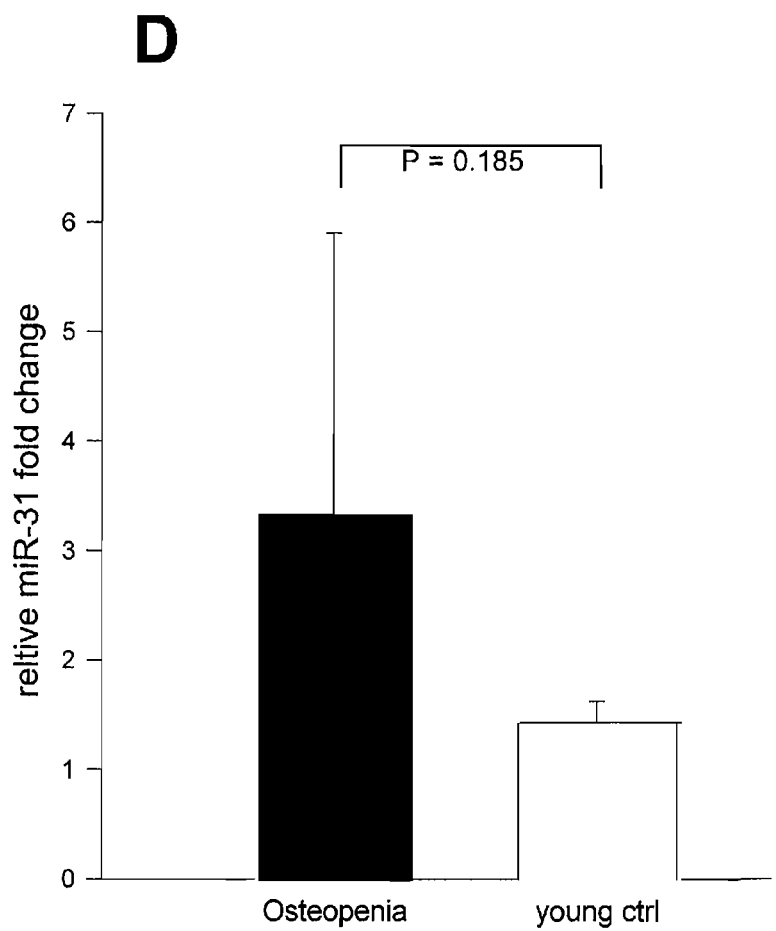

FIG. 8: Exosomes derived from plasma of elderly reduce osteogenic differentiation of ASCs.

(A) Electron microscopy of serum derived exosomes. The image shows typical cup-shaped vesicles of ~50 to 100 nm in diameter. (B) Significant upregualtion of miR-31 levels in serum samples derived form healthy old donors (N=27) compared to young healthy controls (N=21). (C) ASCs were treated with exosomes derived from old and young donors and differentiated into the osteogenic lineage. Differentiation was detected using Alizarin Red staining. Representative pictures of 2 independent experiments are shown. (D) MiR-31 levels in plasma derived from osteopenia patients were significantly increased compared to healthy age matched controls.

Figure 9:
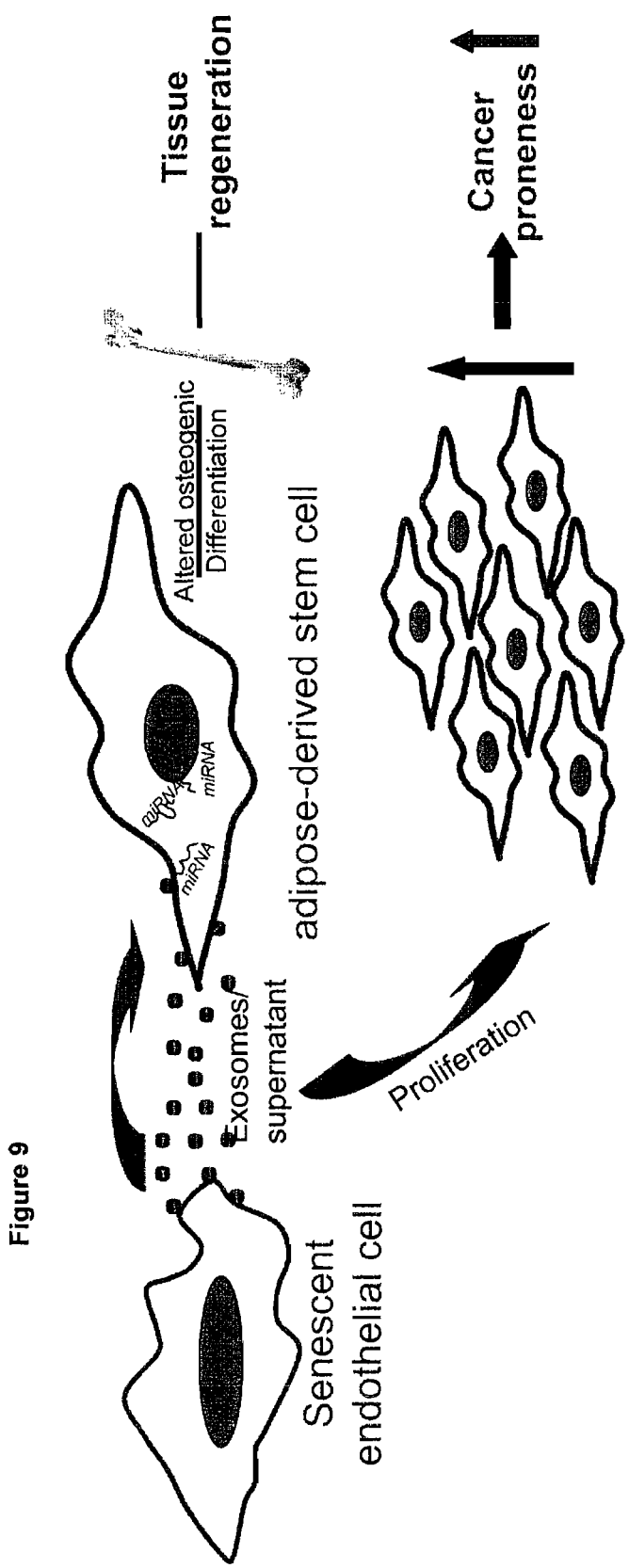

FIG. 9: Proposed model summarizing the results.

Supernatant/exosomes derived from senescent endothelial cells affect proliferation and differentiation potential of ASCs via miRNA delivery. Thereby, the "senescent" environment hampers tissue regeneration and promotes cell growth which is one of the risk factors in the development of cancer.

Figure 10:
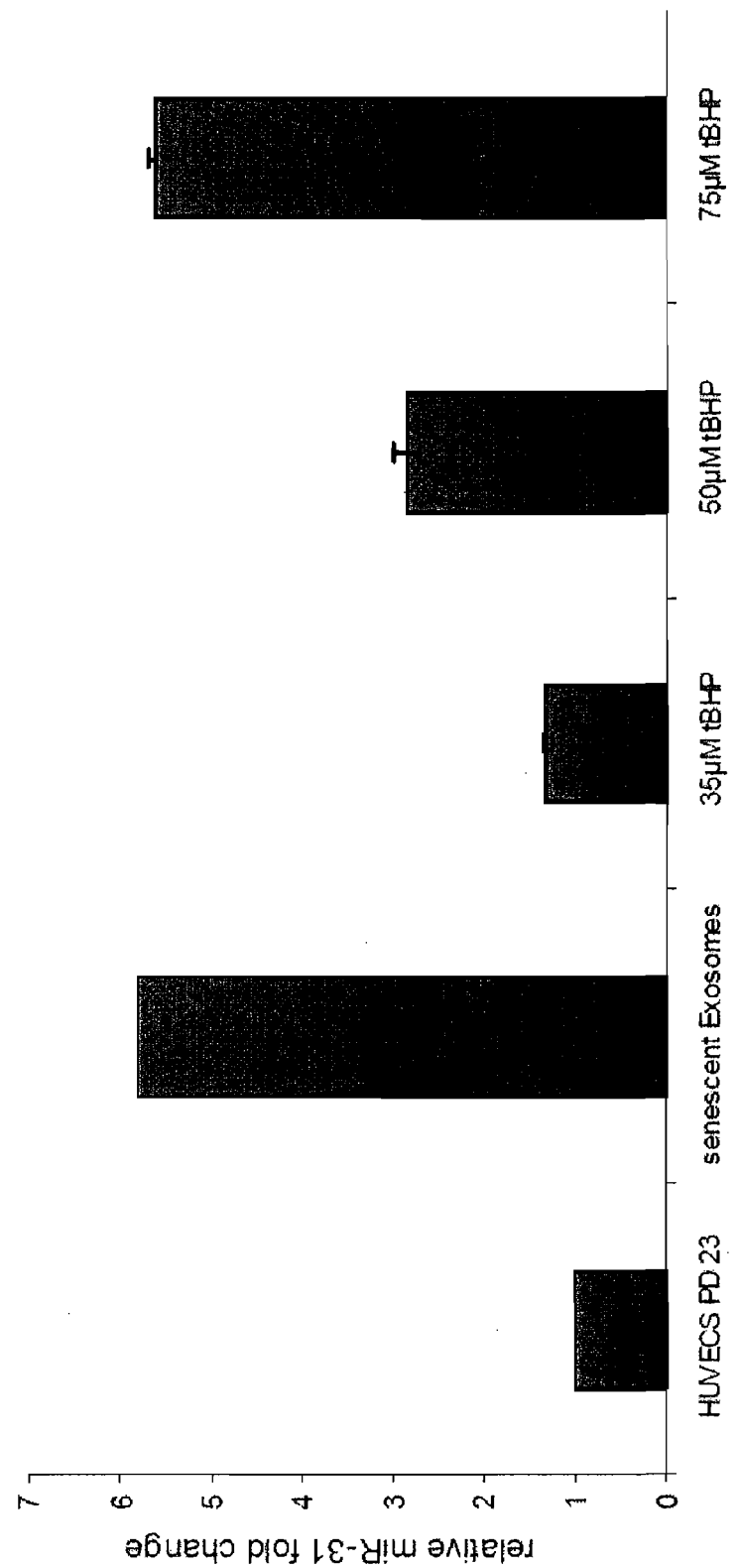

FIG. 10: MiR-31 is also induced by $H_2O_2$ in exosomes derived from senescent versus untreated HUVECs.

Exosomes were harvested from $H_2O_2$ pulsed endothelial cells after 14 days, when no additional cell proliferation was observed in the cells treated with 75 μM tBHP. In contrast, after exposure to 35 μM tBHP the cells completely recovered and resumed growth.

Figure 11:
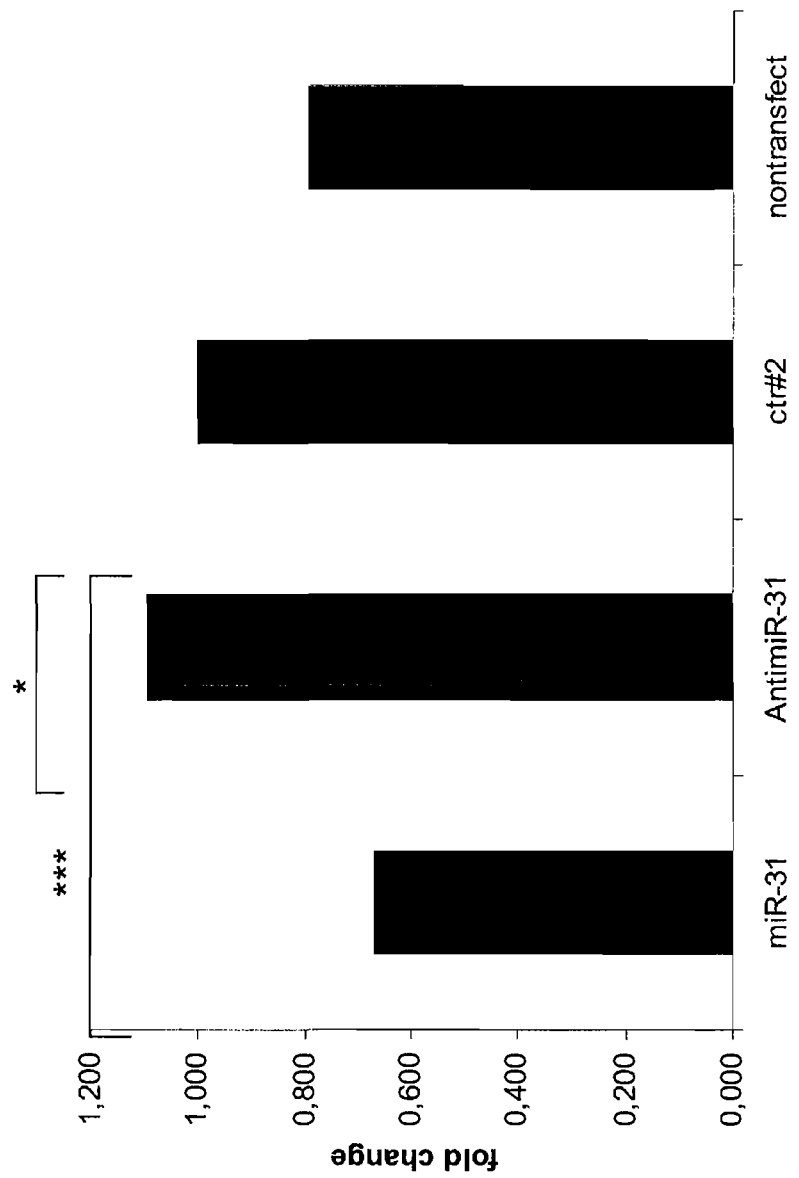

FIG. 11: Levels of osteogenic differentiation of ASCs after transfection with miR-31, anti-miR-31, non-targeting control miRNAs and non-transfected cells.

While miR-31 significantly inhibits osteogenesis as analysed by Alizarin red staining, anti-miR-31 significantly increases osteogenesis.

Figure 12:
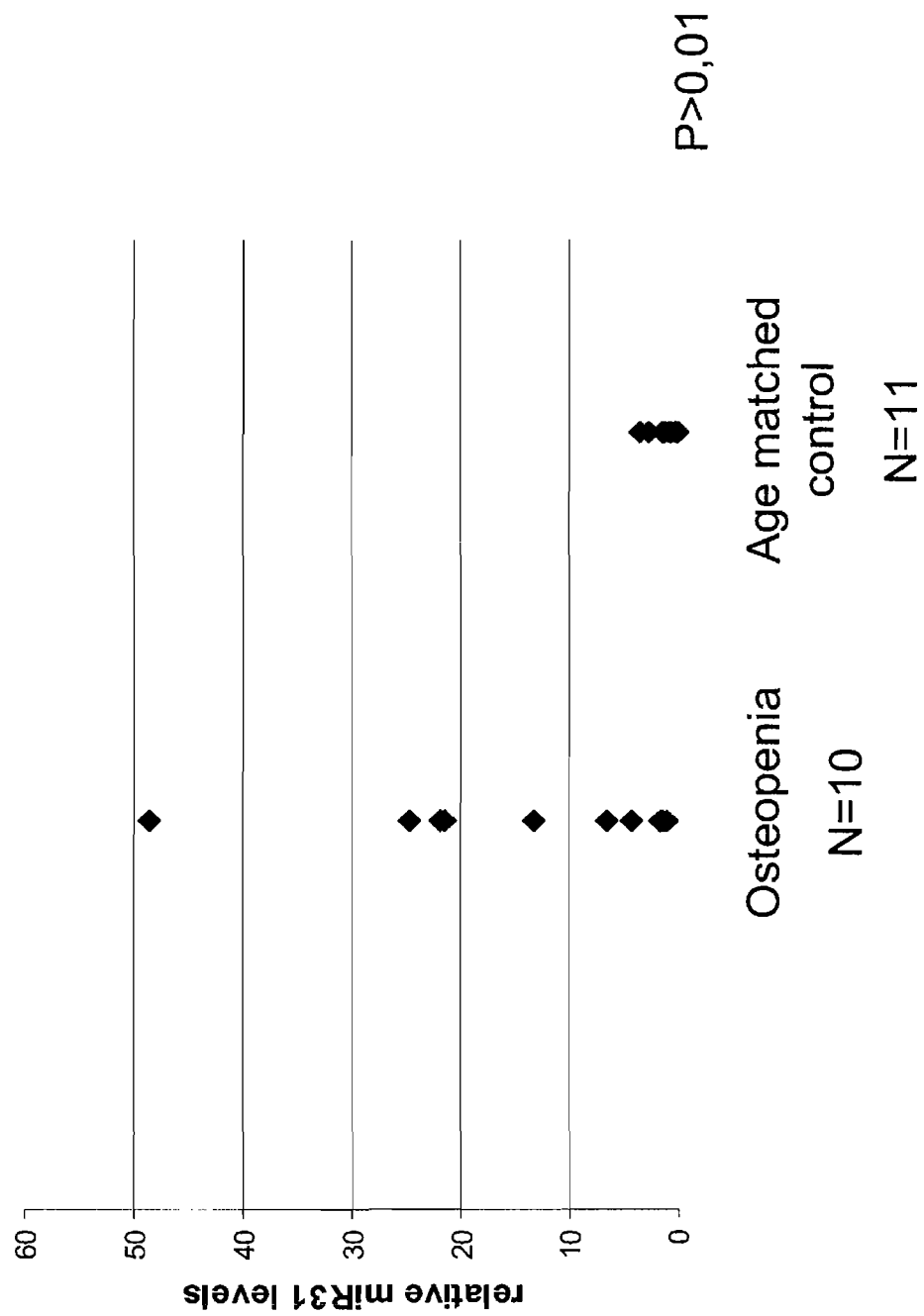

FIG. 12: Plasma levels of miR-31.

Plasma levels of miR-31 of 10 male patients diagnosed with osteopenia were compared to age matched healthy controls. 7 out of 10 patients show higher levels of miR-31 normalized to U6B snRNA, resulting in a highly significant difference as calculated by Student's t testing.

The Examples illustrate the invention.

EXAMPLE 1

Cell Culture

Human Umbilical Vein Endothelial Cell (HUVEC)

Endothelial cells were isolated from human umbilical veins as described (Chang, Exp Cell Res (2005), 309: 121-136; Jaffe, J Clin Invest (1973), 52: 2745-2756). HUVECs were cultivated in gelatin precoated flasks in M199 with Earle's salts supplemented with 4 mM glutamine, 15% fetal calf serum (FCS) and 10% endothelial cell growth supplement (ECGS) containing 170 U/ml heparin at 37° C. in a humidified atmosphere with 5% $CO_2$. Cells were passaged once or twice a week at a split ratio of 1:2 to 1:4 according to the growth rate. HUVECs were cultivated to senescence and stained for senescence associated 3-galactosidase (SA-β-gal) activity as described previously (Chang, loc cit). For collection of supernatants, contact inhibited (quiescent, PD19) and senescent (PD53/95% SA-β-gal positive) cells were allowed to secrete into ASC or HUVEC medium, depending on the experiment, for 48 h. Then supernatants were collected, centrifuged at 1900 g, 4° C. and used freshly for exosome preparation or stored at −80° C. Supernatant volumes were normalized to the number of secreting HUVECs in one flask at the time of supernatant harvest. Cell culture medium incubated for 48 h at 37° C. was used as additional control.

Human Adipose-Derived Stem Cells (ASCs)

Subcutaneous adipose tissue was obtained during outpatient tumescence liposuction under local anestesia. ASCs were isolated as described before (Wolbank, Tissue Eng (2007), 13: 1173-1183; Wolbank, Tissue Eng Part A (2009)) and cultured in DMEM-low glucose/HAM's F-12 supplemented with 4 mM L-glutamine, 10% fetal calf serum (FCS, PAA) and 1 ng/mL recombinant human basic fibroblast growth factor (rhFGF, R&D Systems) at 37° C., 5% $CO_2$ and 95% air humidity. Cells were passaged once or twice a week at a split ratio of 1:2 according to the growth rate. ASCs were characterized due to the expression of specific surface markers (CD13, CD14, CD34, CD45, CD73, CD90, HLA ABC, HLA DR) by flow cytometry (FACS Calibur, Beckton Dickenson) using standard procedures.

Differentiation into Osteogenic Lineage

All differentiation protocols were carried out in 24 well cell culture plates. For osteogenic differentiation, ASCs were seeded at a density of $2 \times 10^3$ cell per well. 72 h after seeding cells were incubated with osteogenic differentiation medium (DMEM-low glucose, 10% FCS, 4 mM L-glutamine, 10 nM dexamethasone, 150 µM ascorbate-2-phosphat, 10 mM (3-glycerolphosphate and 10 nM vitamine-D3) up to 4 weeks.

Alizarin Red Staining

For Alizarin Red staining of calcified structures, cells were fixed for 1 h in 70% ethanol at −20° C. After brief rinsing, cells were stained for 20 min with 40 mM Alizarin Red solution (Sigma) and washed with PBS. For quantification, Alizarin Red was extracted for 30 min using 200 µl 0.1 M HCl/0.5% SDS solution. The extracted dye was measured at 425 nm.

EXAMPLE 2

Transfections

ASCs were transfected using siPORT™ NeoFX™ transfection reagent (Applied Biosystems). Cells were transfected with 10 nM Precursor hsa-miR-31, 100 nM anti-miR-31 or 10 nM negative control 2# (Ambion) according to the manufacturer's protocol. Cells were harvested after 24 or 48 h or differentiation was started as described before three days after transfection.

Moreover, ASCs were transfected with a 0.5 µg dominant negative dynamin construct (K44A) or dynamin wild type construct (provided by Mark A. McNiven Department of Biochemistry and Molecular Biology & Center for Basic Research in Digestive Diseases, Mayo Clinic and Graduate School, Rochester, Minn. 55905, USA) using Metafectene Pro (Biontex Laboratories GmbH) according to manufactures protocol.

EXAMPLE 3

Assessment of Apoptotic Cell Death

HUVECs were seeded in 12-well cell culture plates and were allowed to secrete into ASC medium for 48 h. Thereafter, the cells were detached using 50 mM EDTA and stained with Annexin V-FITC and PI (Roche) according to the manufacturer's instructions. Analysis of the percentage of apoptotic and necrotic/late-apoptotic cells were performed using a FACS-Calibur and the CellQuest software (Becton Dickinson).

EXAMPLE 4

Quantitative Real-Time PCR

Alizarin red stainings were confirmed using different osteogenic differentiation marker genes. Therefore, total ASCs RNA was isolated using Trizol (Invitrogen) at different time points before and during osteogenesis. Reverse transcription was performed using DyNAmo cDNA Synthesis Kit (Biozym) and qPCR was performed using the Rotor-Gene2000 (Corbett). For miRNA analysis, specific TaqMan assays (Applied Biosystems) were used according to manufactures protocol.

For isolation of RNA from blood samples, 250-500 µl serum was used to isolate total RNA using Trizol LS reagent (Invitrogen). To allow for normalization of sample-to-sample variation in RNA isolation, 25 fmol synthetic *C-elegans* miRNAs cel-miR-39 were added before isolation. Serum samples (27 healthy old donors and 21 healthy young donors) were obtained from R. Westendorp, Department of Gerontology & Geriatrics C2-R, Leiden University Medical Center, The Netherlands. Moreover 4 osteopenia serum samples obtained from P. Pietschmann, Department of Pathophysiology, General hospital, Vienna. Institutional ethics committees approved the study, and written, informed consent has been obtained from each subject.

EXAMPLE 5

Lentiviral Transduction

Senenscent HUVECs were transduced with a lentiviral vector containing GFP protein kindly provided by Pidder Jansen-Durr, Institute for Biomedical Aging Research, Innsbruck, Austria (Muck, Rejuvenation Res (2008), 11: 449-453). Briefly, lentiviral transduction was performed using senescent and pre-senescent HUVECs. Generally, 100000-150000 senescent and 50000 pre-senescent HUVECs were plated in a 6-well plate and incubated over night. A multiplicity of infection (MOI) of two to eight with 8 µg/ml Polybrene, which increases the infection efficiency, was used to produce stably transduced cells. As selection pressure, 10 µg/ml Blasticidin was added to the medium. After 6-8 days, clones were stable and contamination with Lentiviral particles was tested by incubation of HeLa's with SN for 4 days. Thereafter, SN was harvested and used for exosomes purification as described before.

EXAMPLE 6

Exosome Purification

Exosomes were purified by filtration and differential centrifugation as described previously (Lehmann, Cancer Res (2008), 68: 7864-7871). In brief, supernatants were collected after incubation of 48 h. This conditioned medium will be centrifuged at 500 g for 10 min to sediment cells and at 14000 g for 15 min to eliminate cell debris and filtered through a 0.22 µm filter excluding a fraction of apoptotic bodies. Exosomes are then sedimented by ultracentifugation at 100000 g for 60 min and the resultant pellet is washed with PBS. Exosomes will be used as fresh preparations for electron microscopy or conserved at −80° C. for further analysis. For differentiation studies, exosomes derived from $2 \times 10^4$ HUVECs in 50 µl PBS were added per well ASCs.

EXAMPLE 7

Electron Microscopy

Purified exosomes were left to settle on nickel coverslips (200 mesh, hexagonal, Pioloform-coated Athene copper grids) After fixation with 4% paraformaldehyd, exosomes were stained with 2% uranyl acetate for 30 sec, coverslips were left to dry and visualized using a transmission electron microscopy (TEM), Philips model CM 12 electron microscope (Philips, Eindhoven, NL).

For electron microscopy, in-situ hybridization (EM-ISH) exosome pellets were permeabilized with 0.1% Triton-X for 5 min at room temperature. After washing with PBS, exosomes were incubated for at least 4 h with hybridization buffer as described previously (Obernosterer, Nat Protoc (2007), 2: 1508-1514). For each sample, 1 pM of the LNA DIG-labelled single stranded probe (Exiqon, Denmark) was denaturated in denaturizing hybridization buffer (containing 50% formamide, 5×SSC, 5×Denhardt's solution, 0.1% Tween, 0.25% CHAPS, 200 µg/ml yeast RNA, 500 µg/ml salmon sperm DNA) by incubation at 80° C. for 5 min. Probes were placed on ice quickly. Exosomes were mixed with the probe and hybridized at 50° C. over night. After hybridization, samples were washed stringently with 0.2×SSC at 60° C. for 1 h. Thereafter, exosomes were incubated with Anti-DIG antibody (Roche) for 30 min and an additional hour with the second 5 nm gold particle labelled antibody (Sigma). After washing with PBS, exosomes were embedded in Epon, sections on average, approximately 80 nm were cut using a Ultramicrotom and were then analysed using transmission electron microscopy (TEM), Philips model CM 12 electron microscope (Philips, Eindhoven, NL).

EXAMPLE 8

Western Blot

Total proteins were extracted and separated on polyacrylamide gels before transfer to a PVDF membrane (Roth, Germany). The membrane was blocked in 5% skimmed milk, incubated with the CD63 antibody (H-193, Santa Cruz) followed by horseradish peroxidase-coupled secondary antibody and subjected to enhanced chemiluminescence using ECL Western Blotting Substrate (Pierce) on a Chemidoc (Biorad).

EXAMPLE 9

Figure 1:
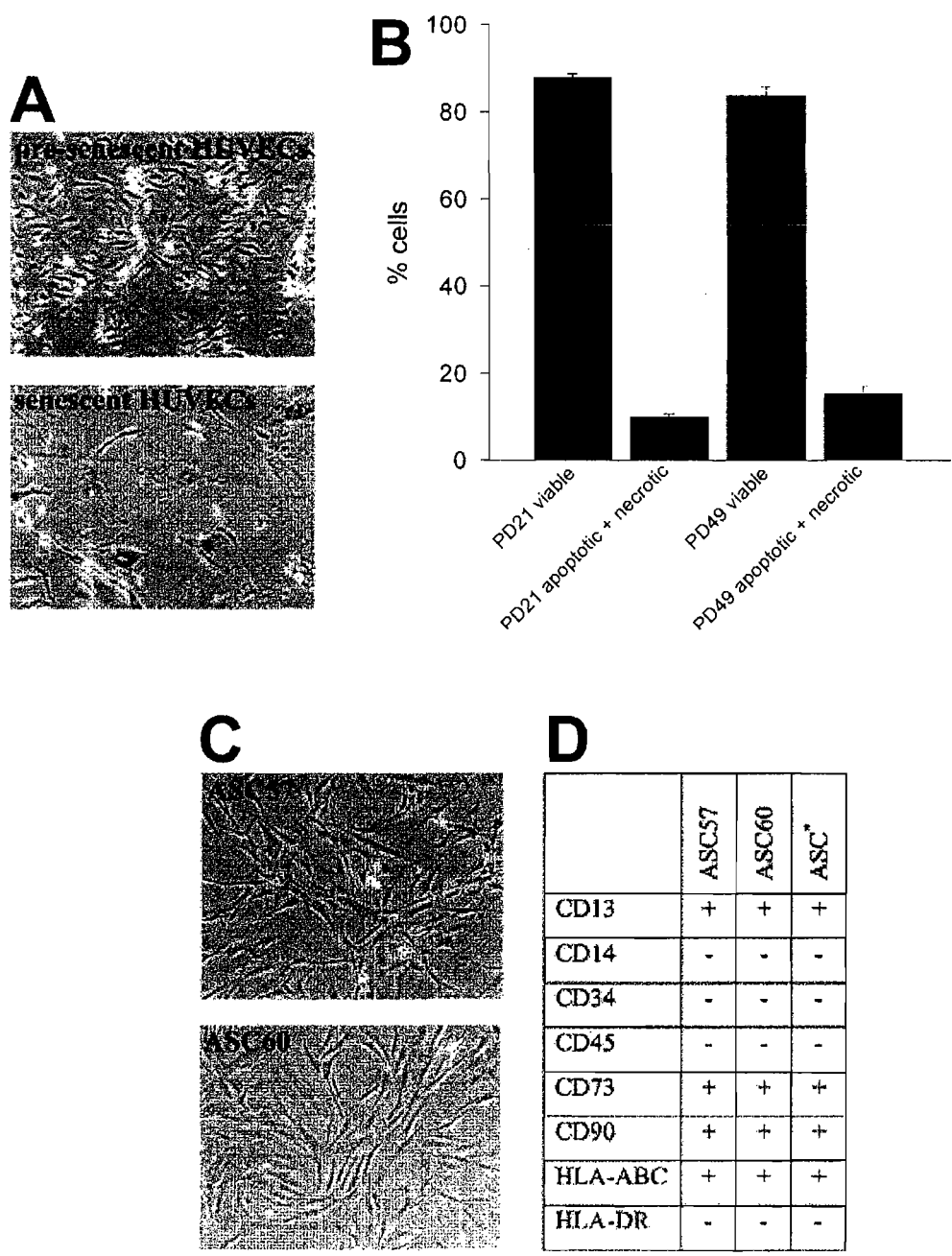
FIG. 1: Characterization of cells and SN used within this study.

Effects of HUVEC Supernatants on Proliferation and Differentiation Apacity of ASCs In order to test if senescent endothelial cells might contribute to the stem cell inhibiting systemic environment (Conboy, Nature (2005), 433: 760-764), well characterized pre-senescent and senescent HUVECs (PDL between PD13 and PD53) were used as established earlier (Chang, Exp Cell Res (2005), 309: 121-136). Senescent cells showed a large flattened morphology and stained positive for SA-β-gal activity (FIG. 1A). In order to produce endothelially secreted factors in ASC medium, endothelial cells were exposed to ASC medium for 48 h. In order to exclude that excessive cell death influences the "secretome", the basal level of cell death of endothelial cells during the time of "harvesting" using Annexin V and PI staining was tested. Their was no significant difference visible between pre-senescent and senescent HUVECs (FIG. 1B).

Furthermore, ASCs showing typical morphology from 6 different donors (examples FIG. 1C) were used and their identity was confirmed by characterization of their surface marker profile (FIG. 1D) as described earlier (Wolbank, 2009, loc cit; Yañez, Stem Cells (2006), 24: 2582-2591).

In order to test and compare the influence of conditioned medium from pre-senescent and senescent HUVECs on growth characteristics of ASCs, cells were incubated with the respective supernatant for a period of 5 d. Although cell viabilities remained unaltered in each test setting throughout the whole experiment (data not shown), ASCs cultivated in the presence of senescent supernatants reached significantly higher cell numbers than cells cultivated in the presence of pre-senescent or control medium (FIG. 2A). Additionally, supernatants derived from senescent cells significantly reduced the osteogenic differentiation potential as stained by Alizarin Red of ASCs after 21 d of incubation with differentiation medium (FIG. 2B).

EXAMPLE 10

Exosomes of Senescent HUVECs Increase Proliferation and Reduce Differentiation Capacity of ASCs Exosomes are membrane coated vesicles, which are between 40 and 100 nm in diameter, and originate from intracellular multivesicular bodies (Pap, Inflamm Res (2009), 58: 1-8). Since recently exosomes have been described as paracrine signalling molecules in various settings (Deregibus, Blood (2007), 110: 2440-2448; Hunter, PLoS ONE (2008), 3: e3694; Lehmann, loc cit; Pap, loc cit), it was tested whether exosomes might contribute to the changes in ASC behaviour. Therefore, exosomes were isolated from HUVEC supernatants by sequential centrifugation steps (Deregibus, loc cit). To confirm the identity of the exosomes electron microscopy was performed. The size distribution strongly indicates that no apoptotic vesicles are visible in our exosome preparations since apoptotic bodies are >500 nm in size (Reich, Exp Cell Res (2009), 315: 760-768) (FIG. 3A). Furthermore, Western blot analysis (FIG. 3B) as well as immunogold labelling (FIG. 3C) using antibodies against CD63 surface protein—a commonly used marker of exosomes (Valadi, Nat Cell Biol (2007), 9: 654-9). (FIG. 3A-C) suggest that the exosome isolation was successful.

When ASCs were treated with exosomes derived from senescent HUVECs, the proliferation rate was again significantly increased (FIG. 3D) compared to stem cells treated with exosomes derived from pre-senescent endothelial cells. Moreover, osteogenic differentiation capacity was significantly decreased by ~50% when cells were treated with senescent exosomes (FIG. 3E), whereas adipogenic differentiation was not influenced (data not shown).

EXAMPLE 11 miR-31 is Secreted by Endothelial Cells

It was shown that beside different proteins, also miRNAs are packed into exosomes (Valadi, loc cit). miR-31 was shown to be upregulated in senescent HUVECs (FIG. 4A). Furthermore, it was tested whether it is also present in HUVEC culture supernatants (FIG. 4B) and exosomes derived from senescent versus pre-senescent endothelial cells (FIG. 4C). Since up to 12-fold changes were detected by qPCR, the localization of miRNAs within exosomes was confirmed by electron microscopy in situ hybridization (EM-ISH). While so far only biochemical assays suggested that miRNAs are inside of exosomes, in context with the present invention, first microscopic proof is provided that miRNAs are indeed packaged into exosomes (FIG. 4D).

EXAMPLE 12

ASCs Take Up Exosomes Derived from HUVECs

In order to test whether endothelial derived miR-31 is taken up by ASCs, ASCs were incubated with SN and exosomes from HUVECs. Indeed, after 48 h a 4-5 fold increase of miR-31 inside of ASCs was observed (FIG. 5A). From these data it was not clear if exosomes are taken up by ASCs or if other components contained within the exosome preparations would induce de novo transcription of miR-31 within ASCs. Therefore, stable transfected senescent endothelial cells expressing GFP (FIG. 5B) were prepared as it was recently published that GFP is packaged into exosomes (Deregibus, loc cit). Two days after incubation with GFP positive exosomes, ASCs showed GFP signals in a punctuate pattern within the cytoplasm while ASCs treated with the supernatant depleted of GFP-exosomes showed no signals (FIG. 5C). To further confirm the exosome uptake, ASCs were transfected with a dominant negative dynamin construct (K44A) and dynamin wild type construct as control (Cao, Mol Biol Cell (1998), 9: 2595-2609; Cao, J Cell Sci (2000), 113 (Pt 11): 1993-2002). Dynamin was shown to be responsible for endocytosis in eukaryotic cells (Cao, 1998, loc cit; Cao, 2000, loc cit) and endocytosis is responsible for uptake of exosomes (Valadi, loc cit). Indeed, as shown in FIG. 5D, miR-31 levels were decreased in ASCs transfected with the dominant negative dynamin construct (K44A).

These results show that miR-31 is indeed taken up via the exosomes and not by induction in consequence of signal transduction through the membrane, it seems that this uptake resembles transfections in vitro, where lipids containing DNA or RNA deliver their cargo into the cells.

EXAMPLE 13 miR-31 Alone Reduces Osteogenic Differentiation of ASCs

In order to investigate the effect of miR-31 alone on differentiation, ASCs were transiently transfected with miR-31. Elevated miR-31 levels were confirmed using TaqMan assay (FIG. 6A). The influence of miR-31 on the differentiation capacity of ASCs was investigated and osteogenic differentiation was significantly inhibited by around 2-fold when ASCs were transiently transfected with miR31 (FIG. 6B), a similar range of inhibition as seen with the exosomes alone. These data indicate that miR-31 is an inhibitor of osteogenic differentiation that might be secreted by endothelial cells especially at senescence.

EXAMPLE 14

Target of miR-31

FZD3 mRNA levels were indicated to be increased in MSCs under osteogenic conditions (Baksh, J Cell Biochem (2007), 101: 1109-1124). In context of the present invention, it was upregulated after 4 days compared to cells treated with control medium (FIG. 7A). Moreover, FZD3 levels were significantly downregulated after treatment with senescent exosomes compared to treatment with young exosomes and control treated cells (FIG. 7B). 24 h after miR-31 transfection, FDZ3 was also downregulated but did not reach significant levels, which might be explained due to the very low mRNA levels of FDZ3 when cells are not differentiating (FIG. 7C). Thus, FZD3 represents not only a marker but also a necessary factor for osteogenic differentiation and might be a direct target of miR-31 also in ASCs.

EXAMPLE 15

Effects of Exosomes Derived from Plasma on ASCs

It was confirmed that exosomes existed in the blood plasma using electron microscopy (FIG. 8A). Then, RNA was isolated from blood serum from 21 healthy young (19-47 years) and 27 old donors (50-91 years) and miR-31 levels were analyzed. As has been found in context of the present invention, they were significantly increased in elderly people and showed larger variations compared to young donors (FIG. 8B). Furthermore, cells were treated with exosomes derived from 1 ml plasma/1 ml medium for 72 h, afterwards differentiation was started. Using 4 different donors, a significant decrease of around 3-fold in osteogenic differentiation of ASCs treated with "old" exosomes (FIG. 8C) was found. The very low differentiation in control samples could be explained by the extremely fast differentiation of the cells treated with exosomes derived from serum. Additionally, herein it was shown that miR-31 levels in plasma derived from osteopenia patients were elevated compared to healthy age matched controls (FIG. 8D).

EXAMPLE 16

Oxidative Stress Induces Senescence

Oxidative stress is known to be associated with endothelial senescence and dysfunction (Seals, Clin Sci (Lond) (2011), 120(9): 357-375). To test whether oxidative stress induces secretion of miR-31, SIPS (stress-induce premature senescence) was induced by tBHP treatment of HUVECs on 5 consecutive days for 1 h each by adding tBHP to a final concentration of 75 µM, 50 µM or 35 µM in the medium. Permanent growth arrest was induced by 75 µM tBHP as assessed by microscopic follow up for 14 d according to the protocols described in Unterluggauer, Exp Gerontol (2003), 38: 1149-1160.

As a result, miR-31 was found to be elevated in exosomes of stress-induced premature senescent endothelial cells. Using increasing doses of $H_2O_2$ (35 µM, 50 µM and 75 µM tButylhydroperoxide (tBHP)), up to 5-fold induction of miR-31 was observed in stress induced senescent HUVECs versus unstressed controls, similar to the levels in replicatively senescent HUVECs (FIG. 10).

Furthermore, the increase of miR-31 in the supernatant of senescent endothelial cells is not restricted to HUVECs that are derived from human umbilical vein endothelial cells, but was also found in senescence of human retinal endothelial cells as well as in senescent human liver derived endothelial cells versus early passage control cells (data not shown).

EXAMPLE 17 miR-31 Antagonist Inhibits Osteogenic Differentiation

In order to test whether miR-31 inhibition improves osteogenic differentiation, antagonistic locked nucleic acids (LNA) against miR-31 were analyzed (Ambion, product ID: AM11465; P/N AM17000). Experimental procedures for transfection of ASCs were performed analogously as done in Example 2 above.

As has been found, a significant increase in Ca-deposition as analysed by Alizarin red staining was observed, while transient increase in miR-31 resulted in decreased osteogenic differentiation (FIG. 11). These data show that inhibition or removal of miR-31 systemically or locally will improve osteoblast formation, e.g., in osteoporosis and after fractures.

EXAMPLE 18 miR-31 Inhibits Osteogenesis in Mouse Model System

In order to confirm that miR-31 is a general regulator of osteogenesis not only in the human system, C3Ht101/2 cell line was used, a mouse mesenchymal multipotent cell line that can be induced to undergo osteogenic differentiation by addition of BMP2 (Richard, PLoS Genetic (2005), 1(6): e74). As readout, cells were co-transfected with a reporter construct encoding luciferase under control of the osteocalcin promoter (Feichtinger, Tissue Eng Part C Methods (2010), 17(4): 401-410).

The influence of miRNA-31 transfection on osteogenic differentiation was furthermore analyzed using the (C2C12) C3Ht10 1/2 cell line in conjunction with an osteocalcin specific reporter gene assay (Feichtinger, Tissue Eng Part C Methods (2010), 17(4): 401-410). (C2C12) C3Ht10 1/2 cells are capable of differentiating to the osteogenic lineage upon treatment with recombinant BMPs, which is observable by the induction of alkaline phosphatase, osteocalcin and other osteoblast specific genes. The cells, seeded in a T175 flask, were first transfected with 99 µg of the osteocalcin reporter system and then 24 h post reverse transfected with 30 nM miRNA-31 or a scrambled miRNA ctrl #12 as control using Ambions siPORT NeoFX. Osteogenic differentiation was induced using 300 ng/ml recombinant BMP2 (InductOS, Pfizer), controls were not induced with growth factor. Osteocalcin reporter activity was assessed after 6 d of differentiation by determining metridia luciferase activity in the cell culture supernatants using Clontech Ready-To-Glow Secreted Luciferase System Kit.

As a result, inhibition of osteogenesis by transient miR-31 overexpression was confirmed also in the mouse model. Furthermore, similar to young versus old healthy humans, it was found that the serum of old mice contains 3-10 fold higher concentrations of miR-31 than the serum of isogenic young mice as controls (data not shown).

EXAMPLE 19

Analysis of miR-31 in Plasma of Osteopenia Patients

Plasma of 10 male patients diagnosed with osteopenia were compared to age matched controls provided by P. Pietschmann, Department of Pathophysiology, General hospital, Vienna. Institutional ethics committees approved the study, and written, informed consent has been obtained from each subject.

Plasma was prepared according to standard procedures clinical procedures as recommended for the analysis of miR-NAs (Taylor, Methods Mol Biol (2011), 728: 235-246; Kroh, Methods (2010), 50: 298-301). Total RNA was isolated using Trizol LS. The qPCR was then performed using Taqman® protocol, where in a first step a specific reverse transcription and then amplification is performed. The amplification of specific miR-31 amplicons is monitored by displacing a fluorescently labelled probe by the amplification. The assays were run in triplicates and differential expression of miR-31 was normalized to the small U6 snRNA. In addition a spike in control of a *C. elegans* specific miRNA was performed to normalize for miRNA recovery during the full RNA isolation—quantification procedure. PCR was performed as detailed below.

TaqMan Protokoll (hsa-miR-31)

Applied Biosystems cDNA Synthesis:

| 2 x mastermix: containing miR-31 and U6 primers volume [µl]: # of reactions: | |
|---|---|
| 100 mM dNTPs | 0.10 |
| MultiScribe RT | 0.60 |
| 10 x Buffer | 1.00 |
| RNase inhibitor | 0.12 |

| 2 x mastermix: containing miR-31 and U6 primers volume [μl]: # of reactions: | |
|---|---|
| Nuclease free water + RNA | 5.18 |
| RT-Primer | 2.00 |
| Total | 9.00 |
| RNA (10 ng/μl) | 1.00 |
| Total | 10.00 |

Program:

16° C.: 30 min

42° C.: 60 min

85° C.: 5 min

4° C.: pause

TaqMan Primer:

Applied Biosystems

| Assay Name | hsa-miR-31 |
|---|---|
| Part Number | 4427975 |
| AB Assay ID | 001100 |

| Assay Type Availability | Mature miRNA Inventoried |
|---|---|

| Mature MicroRNA Details | |
|---|---|
| Mature miRNA Sequence | GGCAAGAUGCUGGCAUAGCUG (SEQ ID NO: 19) |
| Target Species | Gorilla gorilla, *Macaca mulatta*, *Macaca nemestrina*, *Pan paniscus*, *Pongo pygmaeus*, *Pan troglodytes* |
| miRBase ID | ggo-miR-31, mml-miR-31, mne-miR-31, ppa-miR-31, ppy-miR-31, ptr-miR-31 |
| miRBase Accession Number | MIMAT0002381, MIMAT0002379, MIMAT0002383, MIMAT0002384, MIMAT0002382, MIMAT0002380 |
| miRBase Alias | hsa-miR-31 v9.2 |
| Gene Family ID | MIPF0000064, mir-31 |

Device and Software:

Rotor-Gene 6000; Rotor-Gene Software 6000, Series Software 1.7

What is claimed is:

1. A method for diagnosing bone disorders in a subject, which method comprises:
   (a) detecting via a polymerase chain reaction (PCR) method the expression level and/or quantity of miR-31 or of an isoform or variant thereof in a biological sample; and
   (b) comparing the detected expression level and/or quantity of said miR-31 or of said isoform or variants in said biological sample with a corresponding expression level and/or quantity of said miR-31 in a control sample, and
   (c) diagnosing osteoporosis or osteopenia in the subject when a higher expression level and/or quantity of miR-31 is detected in the biological sample than in the control sample,
   wherein a higher expression level and/or quantity of miR-31 detected in the biological sample compared to the control sample is indicative of a risk of developing or having a bone disorder.

2. The method according to claim 1 wherein the expression level and/or quantity of miR-31 or of an isoform or variant thereof is obtained by contacting a biological sample from said subject with a nucleic acid molecule which hybridizes to miR-31 or its 5' or 3' isoforms or variants.

3. The method according to claim 2 wherein the nucleic acid molecule is at least one primer.

4. The method according to claim 3 wherein one primer is a forward primer that is complementary to a sequence of the 5'-end of the polynucleotide to be detected, while another primer is a reverse primer that is complementary to a sequence of the 3'-end of the polynucleotide to be detected.

5. The method according to claim 4 wherein each primer has a length of 12 to 30 nucleotides and is not necessarily 100% complementary to the respective sequence of the polynucleotide to be detected as long as the primer can hybridize to the polynucleotide.

6. The method according to claim 4 wherein the reverse primer is a stem-loop primer which comprises a short overlap with the complement of the target sequence and a stem-loop structure.

7. The method according to claim 4 wherein the primers are conjugated to marker or tagging molecules.

8. The method according to claim 1 further comprising the step of treating osteoporosis or osteopenia in the subject.

9. The method of claim 1, wherein osteopenia is diagnosed in the subject.

10. The method of claim 1, wherein osteoporosis is diagnosed in the subject.

11. The method of claim 8, wherein osteopenia is treated.

12. The method of claim 8, wherein osteoporosis is treated.

* * * * *

SEQUENCE LISTING

```
<160> NUMBER OF SEQ ID NOS: 37

<210> SEQ ID NO 1
<211> LENGTH: 21
<212> TYPE: RNA
<213> ORGANISM: Homo Sapiens

<400> SEQUENCE: 1
aggcaagaug cuggcauagc u                                             21

<210> SEQ ID NO 2
<211> LENGTH: 8
<212> TYPE: RNA
<213> ORGANISM: artificial sequence
<220> FEATURE:
<223> OTHER INFORMATION: seed sequence of miR-31

<400> SEQUENCE: 2 ggcaagau                                                             8

<210> SEQ ID NO 3
<211> LENGTH: 71
<212> TYPE: RNA
<213> ORGANISM: Homo Sapiens

<400> SEQUENCE: 3
ggagaggagg caagaugcug gcauagcugu ugaacuggga accugcuaug ccaacauauu    60
gccaucuuuc c                                                        71

<210> SEQ ID NO 4
<211> LENGTH: 1454
<212> TYPE: DNA
<213> ORGANISM: Homo Sapiens

<400> SEQUENCE: 4
```

```
tttgtcttgt ctaaggtgga atcttgtgc tgtttaaaaa gcagatttta ttctttgcct        60
tttgcatgac tgatagctgt aactcacagt taacatgctt tcagtcaagt acagattgtg      120
tccactggaa aggtaaatga ttgctttttt atattgcatc aaacttggaa catcaaggca      180
tccaaaacac taagaattct atcatcacaa aaataattcg tctttctagg ttatgaagag      240
ataattattt gtctggtaag cattttata aacccactca ttttatattt agaaaaatcc       300
taaatgtgtg gtgactgctt tgtagtgaac tttcatatac tataaactag ttgtgagata      360
acattctggt agctcagtta ataaaacaat ttcagaatta aagaaatttt ctatgcaagg      420
tttacttctc agatgaacag taggactttg tagttttatt tccactaagt gaaaaaagaa      480
ctgtgttttt aaactgtagg agaatttaat aaatcagcaa gggtatttta gctaatagaa      540
taaaagtgca acagaagaat ttgattagtc tatgaaaggt tctcttaaaa ttctatcgaa      600
ataatcttca tgcagagata ttcagggttt ggattagcag tggaataaag agatgggcat      660
tgtttcccct ataattgtgc tgttttata acttttgtaa atattacttt ttctggctgt       720
gtttttataa cttatccata tgcatgatgg aaaaatttta atttgtagcc atcttttccc      780
atgtaatagt attgattcat agagaactta atgttcaaaa tttgctttgt ggaggcatgt      840
aataagataa acatcataca ttataaggta accacaatta caaatggca aaacatttc       900 tctgtattca ttgttgtatt tttctacagt gagatgtgat cttgccaaag ccaccagacc      960
ttggcttcca ggccctcctg tagtgagttg attgtctgca cttgccttgc caatagcca     1020 gtaggctaca gcttttgccc cacacccta ttttcagatt ctggatcatt cttgtttaca     1080
actgaaatat atataacctc agtccaaagt ggtgattgat ttgagtattt gaaaattgtt    1140
gtagctaaat gaagcatgat tagtcttagt atgaatatca tttaatcttt aaaaaatcaa    1200
gtaaaaatgt ttatctgata atgtttaaat aatttacaat ataaactgta aaacttatta    1260
ggcatgaaat caatcagaag agaaagaaaa atgctggaac atgcttgatg tattatgtaa    1320
aaagcatatt taaacaaggg tcctcaaccc tgactgcaga taagaatcac ttgggttact    1380
tcagatgcct aacaccttcc tctcatacaa ataagaattg gtagctttct taaaaaaaaa    1440
aaaaaaaaaa aaaa                                                       1454

<210> SEQ ID NO 5
<211> LENGTH: 19
<212> TYPE: DNA
<213> ORGANISM: artificial sequence
<220> FEATURE:
<223> OTHER INFORMATION: anti-miR-31 (artificial LNA sequence)

<400> SEQUENCE: 5
gctatgccag catcttgcc                                                    19

<210> SEQ ID NO 6
<211> LENGTH: 21
<212> TYPE: RNA
<213> ORGANISM: artificial sequence
<220> FEATURE:
<223> OTHER INFORMATION: complementary sequence

<400> SEQUENCE: 6
agcuaugcca gcaucuugcc u                                                 21

<210> SEQ ID NO 7
<211> LENGTH: 8
<212> TYPE: RNA
<213> ORGANISM: artificial sequence
```

```
<220> FEATURE:
<223> OTHER INFORMATION: complementary sequence

<400> SEQUENCE: 7 aucuugcc                                                                    8

<210> SEQ ID NO 8
<211> LENGTH: 71
<212> TYPE: RNA
<213> ORGANISM: artificial sequence
<220> FEATURE:
<223> OTHER INFORMATION: complementary sequence

<400> SEQUENCE: 8
ggaaagaugg caauauguug gcauagcagg uucccaguuc aacagcuaug ccagcaucuu          60
gccuccucuc c                                                               71

<210> SEQ ID NO 9
<211> LENGTH: 22
<212> TYPE: RNA
<213> ORGANISM: Homo sapiens

<400> SEQUENCE: 9
gaggcaagau gcuggcauag cu                                                   22

<210> SEQ ID NO 10
<211> LENGTH: 22
<212> TYPE: RNA
<213> ORGANISM: Homo sapiens

<400> SEQUENCE: 10
aggcaagaug cuggcauagc ug                                                   22

<210> SEQ ID NO 11
<211> LENGTH: 23
<212> TYPE: RNA
<213> ORGANISM: Homo sapiens

<400> SEQUENCE: 11
aggcaagaug cuggcauagc ugu                                                  23

<210> SEQ ID NO 12
<211> LENGTH: 21
<212> TYPE: RNA
<213> ORGANISM: Homo sapiens

<400> SEQUENCE: 12
aggcaagaug cuggcauagc u                                                    21

<210> SEQ ID NO 13
<211> LENGTH: 20
<212> TYPE: RNA
<213> ORGANISM: Homo sapiens

<400> SEQUENCE: 13
aggcaagaug cuggcauagc                                                      20

<210> SEQ ID NO 14
<211> LENGTH: 19
<212> TYPE: RNA
<213> ORGANISM: Homo sapiens

<400> SEQUENCE: 14
```
aggcaagaug cuggcauag                                                              19

<210> SEQ ID NO 15
<211> LENGTH: 24
<212> TYPE: RNA
<213> ORGANISM: Homo sapiens

<400> SEQUENCE: 15
aggcaagaug cuggcauagc uguu                                                        24

<210> SEQ ID NO 16
<211> LENGTH: 17
<212> TYPE: RNA
<213> ORGANISM: Homo sapiens

<400> SEQUENCE: 16
aggcaagaug cuggcau                                                                17

<210> SEQ ID NO 17
<211> LENGTH: 18
<212> TYPE: RNA
<213> ORGANISM: Homo sapiens

<400> SEQUENCE: 17
aggcaagaug cuggcaua                                                               18

<210> SEQ ID NO 18
<211> LENGTH: 16
<212> TYPE: RNA
<213> ORGANISM: Homo sapiens

<400> SEQUENCE: 18
aggcaagaug cuggca                                                                 16

<210> SEQ ID NO 19
<211> LENGTH: 21
<212> TYPE: RNA
<213> ORGANISM: Homo sapiens

<400> SEQUENCE: 19
ggcaagaugc uggcauagcu g                                                           21

<210> SEQ ID NO 20
<211> LENGTH: 20
<212> TYPE: RNA
<213> ORGANISM: Homo sapiens

<400> SEQUENCE: 20
ggcaagaugc uggcauagcu                                                             20

<210> SEQ ID NO 21
<211> LENGTH: 23
<212> TYPE: RNA
<213> ORGANISM: Homo sapiens

<400> SEQUENCE: 21
ggcaagaugc uggcauagcu guu                                                         23

<210> SEQ ID NO 22
<211> LENGTH: 22
<212> TYPE: RNA
<213> ORGANISM: Homo sapiens

<400> SEQUENCE: 22

```
ggcaagaugc uggcauagcu gu                                        22

<210> SEQ ID NO 23
<211> LENGTH: 23
<212> TYPE: RNA
<213> ORGANISM: Homo sapiens

<400> SEQUENCE: 23
ugcuaugcca acauauugcc auc                                       23

<210> SEQ ID NO 24
<211> LENGTH: 22
<212> TYPE: RNA
<213> ORGANISM: Homo sapiens

<400> SEQUENCE: 24
ugcuaugcca acauauugcc au                                        22

<210> SEQ ID NO 25
<211> LENGTH: 21
<212> TYPE: RNA
<213> ORGANISM: Homo sapiens

<400> SEQUENCE: 25
ugcuaugcca acauauugcc a                                         21

<210> SEQ ID NO 26
<211> LENGTH: 24
<212> TYPE: RNA
<213> ORGANISM: Homo sapiens

<400> SEQUENCE: 26
ugcuaugcca acauauugcc aucu                                      24

<210> SEQ ID NO 27
<211> LENGTH: 22
<212> TYPE: RNA
<213> ORGANISM: Homo sapiens

<400> SEQUENCE: 27
gcuaugccaa cauauugcca uc                                        22

<210> SEQ ID NO 28
<211> LENGTH: 21
<212> TYPE: RNA
<213> ORGANISM: Homo sapiens

<400> SEQUENCE: 28
cuaugccaac auauugccau c                                         21

<210> SEQ ID NO 29
<211> LENGTH: 19
<212> TYPE: DNA
<213> ORGANISM: artificial sequence
<220> FEATURE:
<223> OTHER INFORMATION: forward primer

<400> SEQUENCE: 29
acgcggcaag atgctggca                                            19

<210> SEQ ID NO 30
<211> LENGTH: 19
<212> TYPE: DNA
```

```
<213> ORGANISM: artificial sequence
<220> FEATURE:
<223> OTHER INFORMATION: reverse primer

<400> SEQUENCE: 30
cagtgctggg tccgagtga                                                      19

<210> SEQ ID NO 31
<211> LENGTH: 55
<212> TYPE: DNA
<213> ORGANISM: artificial sequence
<220> FEATURE:
<223> OTHER INFORMATION: primer

<400> SEQUENCE: 31
gtcgtatcca gtgcagggtc cgaggtattc gcactggata cgacagctat gcctg             55

<210> SEQ ID NO 32
<211> LENGTH: 17
<212> TYPE: DNA
<213> ORGANISM: artificial sequence
<220> FEATURE:
<223> OTHER INFORMATION: forward primer

<400> SEQUENCE: 32
tgaccgaggc aagatgc                                                        17

<210> SEQ ID NO 33
<211> LENGTH: 16
<212> TYPE: DNA
<213> ORGANISM: artificial sequence
<220> FEATURE:
<223> OTHER INFORMATION: reverse primer

<400> SEQUENCE: 33
gtgcagggtc cgaggt                                                         16

<210> SEQ ID NO 34
<211> LENGTH: 11
<212> TYPE: RNA
<213> ORGANISM: artificial sequence
<220> FEATURE:
<223> OTHER INFORMATION: seed sequence of MiR-31 plus one nucleotide at
      the 5'-end and two nucleotides at the 3'-end

<400> SEQUENCE: 34
aggcaagaug c                                                              11

<210> SEQ ID NO 35
<211> LENGTH: 10
<212> TYPE: RNA
<213> ORGANISM: artificial sequence
<220> FEATURE:
<223> OTHER INFORMATION: seed sequence of MiR-31 plus one nucleotide at
      the 5'-end and one nucleotide at the 3'-end

<400> SEQUENCE: 35
aggcaagaug                                                                10

<210> SEQ ID NO 36
<211> LENGTH: 10
<212> TYPE: RNA
<213> ORGANISM: artificial sequence
<220> FEATURE:
<223> OTHER INFORMATION: seed sequence of MiR-31 plus one nucleotide at
      the 5'-end and one nucleotide at the 3'-end which has been
      substituted by U
```

```
<400> SEQUENCE: 36
aggcaagauu                                                              10

<210> SEQ ID NO 37
<211> LENGTH: 10
<212> TYPE: RNA
<213> ORGANISM: artificial sequence
<220> FEATURE:
<223> OTHER INFORMATION: seed sequence of MiR-31 plus two nucleotides at
      the 3' -end

<400> SEQUENCE: 37
ggcaagaugc                                                              10
```